(12) United States Patent
Mace et al.

(10) Patent No.: US 7,299,081 B2
(45) Date of Patent: Nov. 20, 2007

(54) ANALYTE TEST DEVICE

(75) Inventors: Chad Harold Mace, Hudson, NH (US);
Andrea Nicolaisen, Arlington, MA (US); Damon H. Dehart, Bedford, MA (US)

(73) Assignee: Abbott Laboratories, Abbott Park, IL (US)

( * ) Notice: Subject to any disclaimer, the term of this patent is extended or adjusted under 35 U.S.C. 154(b) by 211 days.

(21) Appl. No.: 10/868,575

(22) Filed: Jun. 15, 2004

(65) Prior Publication Data

US 2005/0277850 A1    Dec. 15, 2005

(51) Int. Cl.
*A61B 5/05*     (2006.01)
*A61B 5/00*     (2006.01)
*A61B 17/3209*  (2006.01)
*G01N 27/26*    (2006.01)

(52) U.S. Cl. .................. 600/345; 600/347; 600/365; 600/573; 606/182; 204/403.01

(58) Field of Classification Search ............ 204/403.02
See application file for complete search history.

(56) References Cited

U.S. PATENT DOCUMENTS

| | | | |
|---|---|---|---|
| 5,540,709 A * | 7/1996 | Ramel | 600/183 |
| 6,071,294 A * | 6/2000 | Simons et al. | 606/181 |
| 6,093,156 A * | 7/2000 | Cunningham et al. | 600/573 |
| 6,332,871 B1 * | 12/2001 | Douglas et al. | 600/583 |
| 6,349,229 B1 * | 2/2002 | Watanabe et al. | 606/345 |
| 6,506,168 B1 | 1/2003 | Fathallah et al. | |

(Continued)

FOREIGN PATENT DOCUMENTS

| EP | 0 747 006 | 12/1996 |
|---|---|---|
| EP | 1 285 629 | 2/2003 |

(Continued)

OTHER PUBLICATIONS

The PCT Search Report.

*Primary Examiner*—Charles A. Marmor, II
*Assistant Examiner*—Patricia C. Mallari
(74) *Attorney, Agent, or Firm*—Jackson & Co., LLP; Andrew V. Smith

(57) ABSTRACT

An analyte test device is constructed as an integrated, single-use, disposable cartridge which can be releasably installed into a compatible analyte test monitor. In use, the device can be used in conjunction with the monitor to lance the skin of a patient to create a blood sample and, in turn, calculate the concentration of a particular analyte in the expressed blood sample. In one embodiment, the device includes a base and a cover which are affixed together to create a test cartridge which has a substantially flat and low profile design. A lancet carrier is disposed between the base and the cover and includes a anchor fixedly mounted on the base and a lancet support member which is slidably mounted on the base, the anchor and the lancet support member being connected by a spring. A lancet is removably mounted on the lancet support member is disposed directly beneath an analyte test strip which secured to the underside of the cover. In another embodiment, the device includes a cylindrical housing with an open top end and an open bottom end. A spring biased lancet is slidably mounted within the cylindrical housing. An analyte test strip is fixedly mounted within the cylindrical housing and is disposed at an acute angle relative to the lancet.

15 Claims, 16 Drawing Sheets

U.S. PATENT DOCUMENTS

| | | |
|---|---|---|
| 6,561,989 B2 * | 5/2003 | Whitson ..................... 600/573 |
| 6,849,052 B2 * | 2/2005 | Uchigaki et al. ........... 600/584 |
| 2002/0177761 A1 * | 11/2002 | Orloff et al. ................ 600/309 |

FOREIGN PATENT DOCUMENTS

| | | |
|---|---|---|
| EP | 1285629 A1 * | 2/2003 |
| WO | 98/35225 | 8/1998 |

* cited by examiner

US 7,299,081 B2

ANALYTE TEST DEVICE

BACKGROUND OF THE INVENTION

The present invention relates generally to integrated lancing and analytical devices and more particularly to a novel integrated lancing and analytical device.

There are many medical conditions which require frequent measurement of the concentration of a particular analyte in the blood of a patient. For example, diabetes is a disease which typically requires a patient to routinely measure the concentration of glucose in his/her blood. Based upon the results of each blood glucose measurement, the patient may then require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

A multi-step process is commonly practiced by diabetes patients to self-monitor the level of glucose present in their blood.

In the first step of said process, a patient is required to provide a blood sample suitable for testing. Blood samples taken from a patient for blood sugar monitoring are typically obtained by piercing the skin of the patient using a lancet device. A lancet device typically includes a body and a lancet. The body is typically adapted to be held by the user, the lancet being coupled to the body and being adapted to penetrate through the epidermis (the outermost layer of the skin) of the patient and into the dermis (the layer of skin directly beneath the epidermis) which is replete with capillary beds. The puncture of one or more capillaries by the lancet generates a sample of blood which exits through the incision in the patient's skin.

In some lancet devices, the lancet extends from the body at all times. In other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position (e.g., using a spring) in order to minimize the risk of inadvertent lancet sticks.

In the second step of said process, a blood glucose monitoring system is utilized to measure the concentration of glucose in the blood sample. One type of glucose monitoring system which is well known and widely used in the art includes a blood glucose meter (also commonly referred to a blood glucose monitor) and a plurality of individual, disposable, electrochemical test strips which can be removably loaded into the meter. Examples of blood glucose monitoring systems of the type described above are manufactured and sold by Abbott Laboratories, Medisense Products of Bedford, Mass. under the PRECISION line of blood glucose monitoring systems.

Each individual electrochemical test strip typically includes a substrate which is formed as a thin, rectangular strip of non-conductive material, such as plastic. A plurality of carbon-layer electrodes are deposited on the substrate along a portion of its length in a spaced apart relationship, one electrode serving as the reference electrode for the test strip and another electrode serving as the working electrode for the test strip. All of the conductive electrodes terminate at one end to form a reaction area for the test strip. In the reaction area, an enzyme is deposited on the working electrode. When exposed to the enzyme, glucose present in a blood sample undergoes a chemical reaction which produces a measurable electrical response. The other ends of the electrical contacts are disposed to electrically contact associated conductors located in the blood glucose monitor, as will be described further below.

A blood glucose monitor is typically modular and portable in construction to facilitate its frequent handling by the patient. A blood glucose monitor often comprises a multifunction test port which is adapted to receive the test strip in such a manner so that an electrical communication path is established therebetween. As such, an electrical reaction created by depositing a blood sample onto the reaction area of the test strip travels along the working electrode of the test strip and into the test port of the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, the blood glucose monitoring system of the type described above can be used in the following manner to measure the glucose level of a blood sample and, in turn, store the result of said measurement into memory as test data. Specifically, a disposable test strip is unwrapped from its packaging and is inserted into the test port of the monitor. With the test strip properly inserted into the monitor, there is established a direct electrical contact between the conductors on the test strip and the conductors contained within the test port, thereby establishing an electrical communication path between the test strip and the monitor. Having properly disposed the test strip into the test port, the monitor typically displays a "ready" indication on its display.

The user is then required to provide a blood sample using a lancet device. Specifically, a disposable lancet is unwrapped from its protective packaging and is loaded into a corresponding lancet device. The lancet device is then loaded, if necessary, and fired into the skin of the patient to provide a blood sample.

After lancing the skin, the patient is required to deposit one or more drops of blood from the patient's wound site onto the reaction area of the test strip. When a sufficient quantity of blood is deposited on the reaction area of the test strip, an electrochemical reaction occurs between glucose in the blood sample and the enzyme deposited on the working electrode which, in turn, produces an electrical current which decays exponentially over time. The decaying electrical current created through the chemical reaction between the enzyme and the glucose molecules in the blood sample, in turn, travels along the electrically conductive path established between the test strip and the monitor and is measured by the microprocessor of the monitor. The microprocessor of the monitor, in turn, correlates the declining current to a standard numerical glucose value (e.g., using a scaling factor). The numerical glucose value calculated by the monitor is then shown on the monitor display for the patient to observe. In addition, the data associated with the particular blood glucose measurement is stored into the memory for the monitor.

A principal drawback associated with diabetes management systems of the type described above is that the lancing and glucose measurement operations are performed independently of one another. As a result, the user is required to possess both a lancet device and a blood glucose test monitor (as well as an individually packaged lancet and test strip) in order to perform a single assay. Furthermore, because the lancing and glucose measurement operations are performed independently of one another, the aforementioned process for performing an assay is relatively complicated and requires a considerably high level of manual dexterity, which is highly undesirable.

Accordingly, some diabetes management systems presently available in the market include a single blood glucose test device which is capable of performing both the lancing and glucose measurement operations. One type of glucose monitoring system which includes a single device for performing both the lancing and glucose measurement operations is manufactured and sold by Abbott Laboratories, Medisense Products of Bedford, Mass. under the SOF-TACT™ line of diabetes management systems. The SOF-TACT™ blood glucose meter is represented, inter alia, in U.S. Pat. No. 6,506,168, which is incorporated herein by reference.

The SOF-TACT™ blood glucose meter is adapted to receive both a single disposable lancet and a single disposable test strip. In order to prepare the meter for an assay, the patient is required to open a pivotally mounted cover. With the cover opened, the patient is required to unwrap an individually sealed lancet and, in turn, mount the unwrapped lancet in a cylindrical lancet holder. In addition, the patient is required to unwrap an individually sealed test strip and, in turn, insert the unwrapped test strip into a test strip port. With a lancet and a test strip installed into the meter as described above, the cover is pivoted closed. To commence an assay, the patient positions a specified region of the monitor against his/her skin and presses an activation button. Depression of the activation button creates a pressure gradient which drives the lancet through an opening in the pivotable cover and into the patient's skin. The pressure gradient is then removed which retracts the lancet to its original unfired position.

After an opening has been formed in the skin of the patient, the blood sample is collected so that an assay can be performed. Specifically, a vacuum pump is used to draw blood from the wound site and in the direction towards the test strip. Simultaneously, mechanical linkages within the monitor use pressure to move the test strip towards the opening in the pivotable cover such that blood emerging from the patient's skin collects onto the reaction area of the test strip. When a sufficient amount of blood has been collected, the vacuum pump is deactivated. The meter then performs the assay based upon the electrochemical signal generated by the test strip and displays the result on an LCD screen.

Upon completion of the assay, the user is required to pivot open the cover of the meter and remove the used test strip and lancet. Because each test strip and lancet is designed for a single-use, the used test strip and lancet are discarded. The cover is then closed until future tests are required, at which time, the above-described process is repeated.

Although the SOF-TACT™ blood glucose meter effectively combines both lancing and measurement processes into a single device, the user is still required to store and use two separate disposable products (i.e., a lancet and a test strip) in order to perform a single assay. As can be appreciated, the requirement that the user store, unwrap, load and discard two separate disposable items into the device renders this system still somewhat complex to use.

Accordingly, some diabetes management systems which are known in the art require only the following two items in order to complete a blood glucose test: (1) a single, reusable blood glucose test device (or monitor) and (2) an integrated, disposable, single-use test cartridge for use in conjunction with the blood glucose test device. The integrated disposable test cartridge (commonly referred to in the art as an analyte test device, an integrated lancing and analytical device or simply as an integrated disposable) includes both a lancet and an electrochemical test strip.

For example, in U.S. Pat. No. 6,561,989, there is disclosed an integrated disposable end cap which can used in conjunction with an associated blood glucose monitoring device. The integrated disposable end cap includes a thin test sensor and a thin lance which are coupled together. The thin lance is formed from a single piece of metal and includes a base and a thin needle which are connected by a thin spring.

As can be appreciated, the principal benefit of a system which uses an integrated disposable end cap in conjunction with a corresponding blood glucose monitoring device is the simplicity in which a patient can perform an assay. Specifically, a patient is required only to unwrap and load a single integrated disposable end cap onto the corresponding test device prior to performing the assay. When an assay is required, the user is only required to place his/her finger against a particular region of the integrated disposable end cap and, subsequent thereto, depress a suitable trigger or button in order to actuate both the lancing and blood analysis operations. As a result, the number and relative complexity of steps which the patient is required to perform is significantly reduced, which is highly desirable.

The integrated disposable end cap described in detail above suffers from a couple notable drawbacks in its design.

As a first drawback, the integrated disposable end cap described in detail above includes a thin lance which is constructed from a single piece of metal. Because the shape of the sharpened needle is integrated directly into the overall shape of the lance, it is to be understood that alternative types of needles configurations (e.g., multi-tip needles) can not be readily integrated into this particular end cap without necessitating a complete reconstruction of the entire thin lance, which is highly undesirable.

As a second drawback, the integrated disposable end cap described in detail above is not substantially enclosed. As a result, the end cap is highly susceptible to the contamination of its lancet and/or test sensor prior to use (e.g., by moisture), which is highly undesirable.

SUMMARY OF THE INVENTION

It is an object of the present invention to provide a novel analyte test device.

It is another object of the present invention to provide a novel analyte test device which can be removably installed into a compatible analyte test monitor.

It is yet another object of the present invention to provide a novel analyte test device of the type described above which, in conjunction with said compatible analyte test monitor, can be used to draw a blood sample and, in turn, measure the concentration of a particular analyte in said blood sample.

It is still another object of the present invention to provide an analyte test device of the type described above which includes a sharpened needle for drawing an adequate blood sample with minimal discomfort to the patient.

It is yet still another object of the present invention to provide an analyte test device of the type described above which readily allows for modifications to the particular geometry of the sharpened needle.

It is another object of the present invention to provide an analyte test device of the type described above which is designed to minimize the possibility of contamination.

It is yet another object of the present invention to provide an analyte test device of the type described above which has a limited number of parts, which is inexpensive to manufacture and which is easy to use.

Therefore, according to one feature of the present invention, there is provided an analyte test device which is adapted to be removably coupled to a compatible analyte test meter, said analyte test device comprising a base, said base including a top surface, a bottom surface, a front end and a rear end, a cover removably affixed to said base, said cover including a top surface, a bottom surface, a front end and a rear end, a lancet carrier disposed between said base and said cover, said lancet carrier comprising a spring, the spring having a first end and a second end, the first end of the spring being fixedly coupled to said base, the second end of the spring capable of displacement relative to the first end, a lancet removably mounted on said lancet carrier, and an analyte test strip disposed between said base and said cover, said analyte test strip having a first end, a second end and a plurality of electrodes.

According to another feature of the present invention, there is provided an analyte test device which is adapted to be removably coupled to a compatible analyte test meter, said analyte test device comprising a base, said base including a top surface, a bottom surface, a front end and a rear end, a lancet removably mounted on said base, an analyte test strip mounted on said base over said lancet, said analyte test strip comprising a first end, a second end and a plurality of electrodes, and a housing, said housing including a top surface, a bottom surface, a front end, a rear end and a pair of sidewalls which together define a substantially enclosed interior cavity, the interior cavity being sized and shaped to receive said base, said lancet and said analyte test strip.

According to another feature of the present invention, there is provided an analyte test device which is adapted to be removably coupled to a compatible analyte test meter, said analyte test device comprising a housing shaped to define an interior cavity, a lancet slidably mounted within the interior cavity of said housing, said lancet comprising a sharpened tip, the sharpened tip being adapted to selectively penetrate outside of the interior cavity of said housing, and an analyte test strip disposed within the interior cavity of said housing at an acute angle relative to said lancet, said analyte test strip comprising a first end, a second end and a plurality of electrodes.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
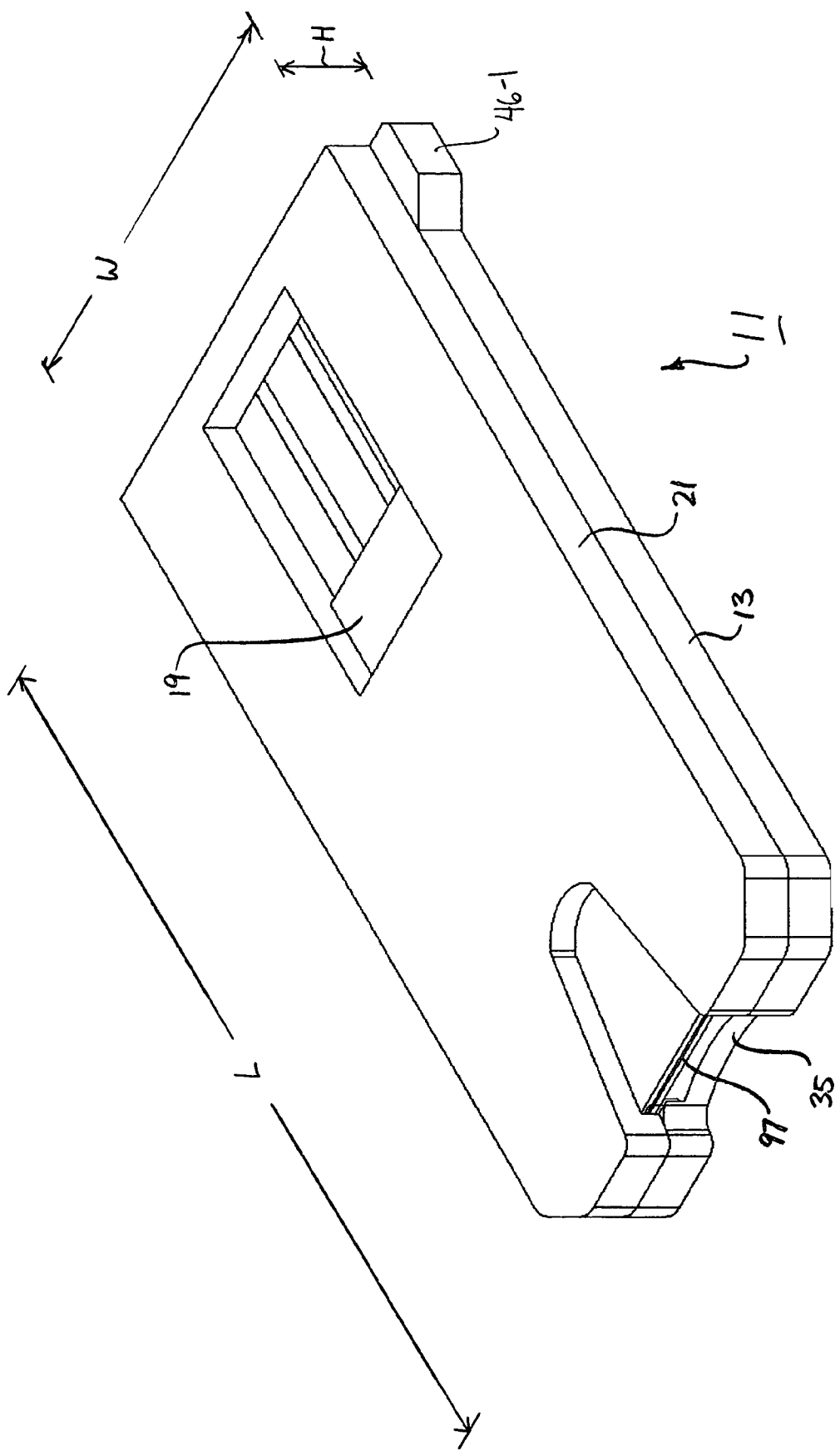
FIG. 1 is a top, front, right side perspective view of a first embodiment of an analyte test device which is constructed according to the teachings of the present invention.

Referring now to the drawings, there is shown in FIGS. 1-5 a first embodiment of an analyte test device which is constructed according to the teachings of the present invention, the device being identified generally by reference numeral 11. As will be described further in detail below, device 11 is constructed as a unitary, single-use, disposable cartridge which is adapted to be releasably installed into a compatible analyte test monitor (also referred to herein as an analyte test meter). In conjunction with said analyte test monitor, device 11 is capable of performing both (1) a lancing operation on the skin of a patient in order to draw a sample of blood and (2) an analysis of the concentration of a particular analyte in said blood sample. Because device 11 can be used in conjunction with an analyte test monitor to perform both lancing and analyte concentration measurements, device 11 is also referred to herein as an integrated lancing and analytical device (or simply as an integrated disposable).

Device 11 comprises a base 13, a lancet carrier 15 secured at one end to base 13, a lancet 17 mounted on lancet carrier 15, an analyte test strip 19 disposed directly above lancet carrier 15 and lancet 17, and a cover 21 secured to base 13 over lancet carrier 15, lancet 17 and test strip 19 to create a unitary, substantially enclosed, disposable test cartridge which preferably has a length L of approximately 27 mm, a width W of approximately 12.5 mm and a height H of approximately 3 mm. Preferably, device 11 can be mass produced with each individual device 11 enclosed within a hermetically-sealed package to protect against contamination, humidity and inadvertent lancing.

It should be noted that device 11 is provided with a substantially flat, low profile design. As a result, multiple devices 11 can be stacked vertically on top of each other in a relatively confined area, which is highly desirable.

Figure 4:
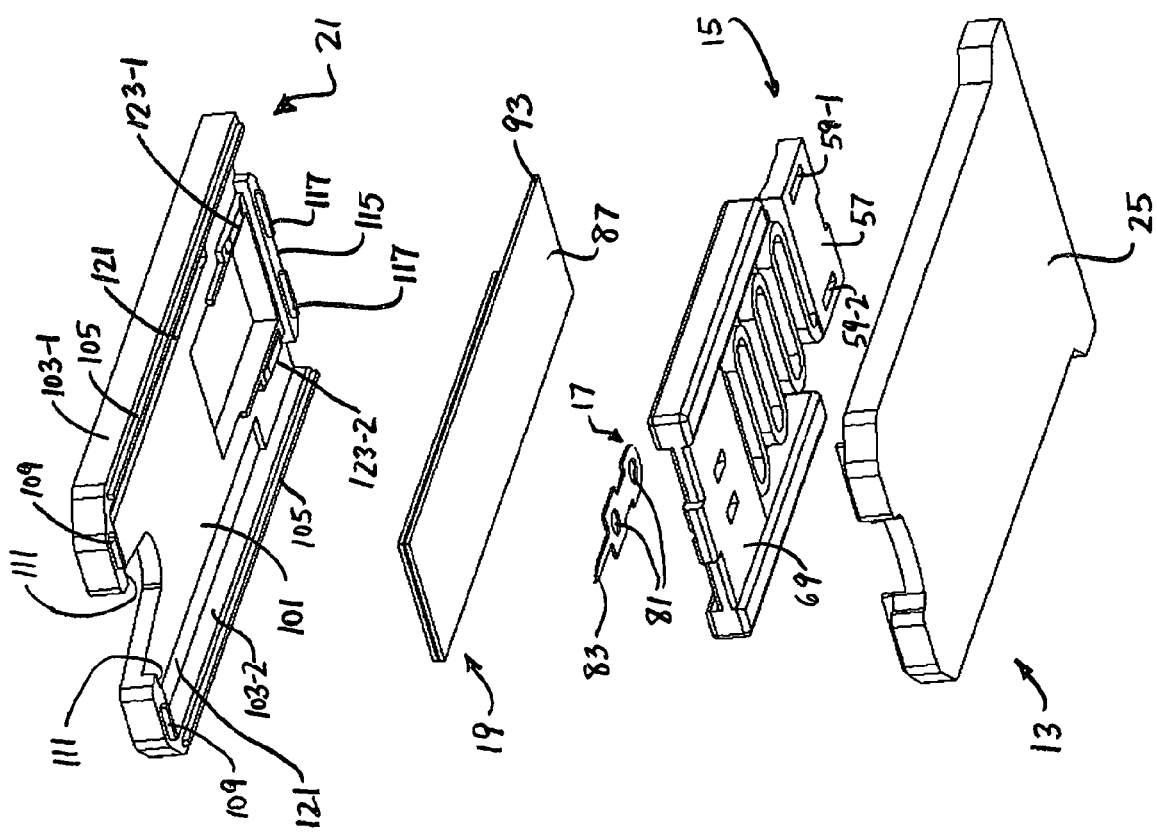
FIG. 4 is a bottom, front, right side exploded perspective view of the device shown in FIG. 1.
Figure 5:
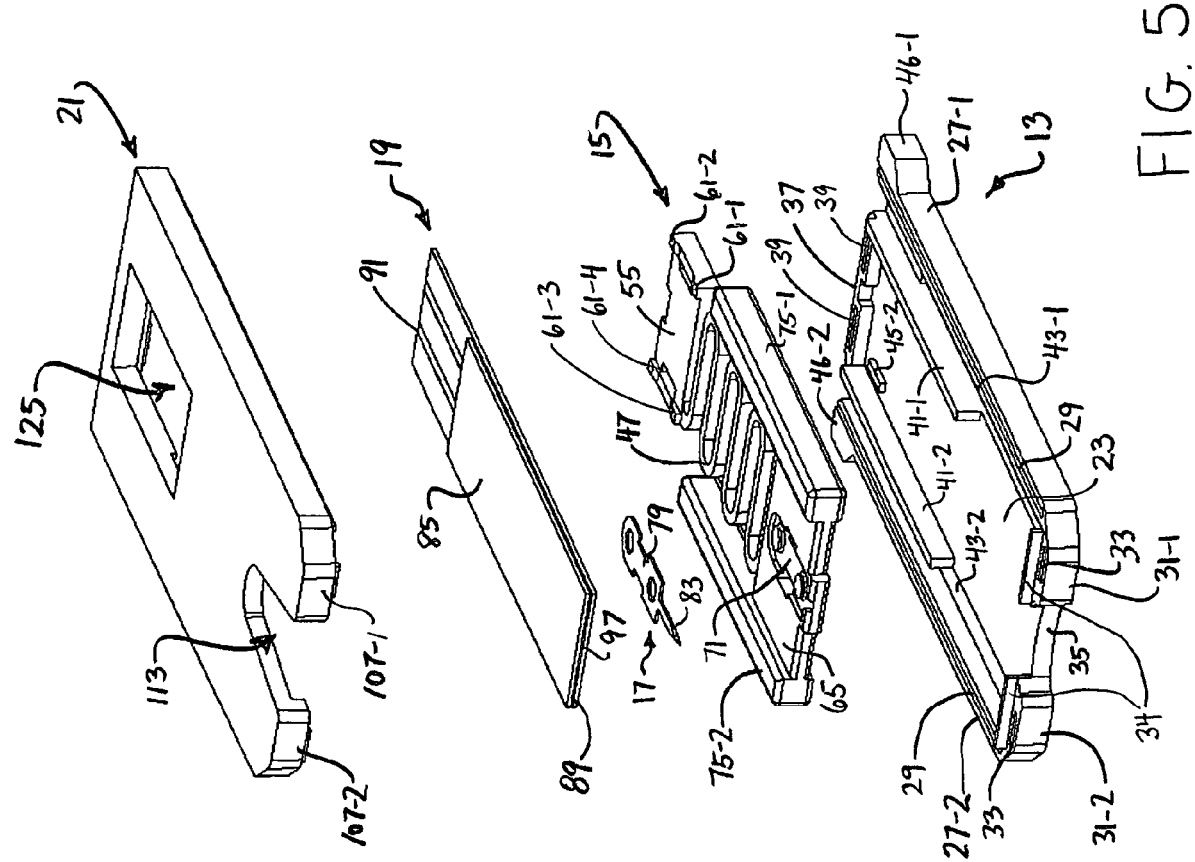
FIG. 5 is a top, front, right side exploded perspective view of the device shown in FIG. 1.

As seen most clearly in FIGS. 4 and 5, base 13 is a unitary member which is preferably constructed of a rigid and durable plastic material using conventional molding techniques. Base 13 includes a substantially flat top surface 23 and a substantially flat bottom surface 25.

A pair of elongated sidewalls 27-1 and 27-2 extends orthogonally upward from top surface 23 and are positioned along the length of the right and left side edges, respectively, of base 13. A longitudinal groove 29 is formed into the top surface of each sidewall 27 and serves to facilitate in securing cover 21 onto base 13, as will be described further below.

A pair of spaced apart front walls 31-1 and 31-2 extends orthogonally upward from top surface 23 and are positioned along the front edge of base 13. A shortened groove 33 is formed into the top surface of each front wall 31 and serves to facilitate in securing cover 21 onto base 13, as will be described further below. In addition, a raised abutment surface 34 is formed along the rear surface of each front wall 31, abutment surfaces 34 serving to limit the forward displacement of lancet carrier 15 during the lancing operation, as will be described further below.

It should be noted that a skin receiving surface 35 is formed into the front edge of base 13 between front walls 31-1 and 31-2. Skin receiving surface 35 is represented herein as being in the form of an inwardly extending arcuate notch. However, it is to be understood that surface 35 is not limited to having an arcuate configuration. Rather, it is to be understood that surface 35 could have an alternative contour (e.g., a squared-off, or stepped, contour with multiple flat surfaces) without departing from the spirit of the present invention.

In use, a patient is required to place an area of his/her body (e.g., a finger, forearm, thigh, etc.) against the front of device 11 prior to commencing the lancing and blood analysis processes, as will be described further in detail below. It should be noted that the particular shape of skin receiving surface 35 provides a couple of notable advantages.

As a first advantage, the inward contour of skin receiving surface 35 causes the region of the patient's skin that is pressed thereagainst device 11 to bulge and distend. As a result, surface 35 serves to increase the amount of blood present in the patient's skin at the wound site just prior to the lancing procedure, which is highly desirable.

As a second advantage, the inward contour of skin receiving surface 35 prevents the wound site to be created in the patient's skin from contacting base 13. Rather, the wound site for the patient is drawn into contact against analyte test strip 19. As a result, blood expressed from the wound site is drawn onto test strip 19 and not onto base 13, which is highly desirable.

A shortened rear wall 37 extends orthogonally upward from top surface 23 and is positioned along a portion of the rear edge of base 13. A pair of spaced apart grooves 39 is formed into the top surface of rear wall 37 and serves to facilitate in securing cover 21 onto base 13, as will be described further below.

A pair of spaced apart and parallel partitions 41-1 and 41-2 extends orthogonally upward from top surface 23. Partitions 41 protrude forward from rear wall 37 approximately half the length of base 13, each partition 41 being spaced adequately in from a corresponding sidewall 27 in a parallel relationship. Furthermore, a pair of longitudinal recesses 43-1 and 43-2 is formed into top surface 23 and extend rearward from abutment surfaces 34 for the majority of the length of base 13, recess 43-1 being formed between sidewall 27-1 and partition 41-1 and recess 43-2 being formed between sidewall 27-2 and partition 41-2. As will be described further below, sidewalls 27, partitions 41 and recesses 43 limit the displacement of one end of carrier 15 relative to base 13 along a linear path.

A pair of shortened tabs 45-1 and 45-2 extends orthogonally upward from top surface 23 and is positioned between partitions 41 and along rear wall 37. As will be described further below, each tab 45 is sized and shaped to fittingly protrude through a corresponding slot in carrier 15 in order to fixedly secure one end of carrier 15 to base 13.

In addition, a pair of outwardly extending wings 46-1 and 46-2 are formed onto sidewalls 27-1 and 27-2, respectively, along the rear of base 13. As will be described further below, wings 46 serve two principal functions: (1) to provide device 11 with a keyed-type lateral cross-section along its rear end, thereby ensuring the installation of device 11 within a compatible blood glucose monitor in the proper orientation, and (2) to ensure that device 11 is suitably retained (i.e., locked) within the compatible blood glucose monitor when installed therein.

Lancet carrier 15 is a unitary and substantially flat member that is constructed out of a rigid and durable plastic material using conventional molding techniques. Lancet carrier 15 is shaped to include a spring 47 comprising a first end 49 and a second end 51.

A rectangular anchor 53 is integrally formed onto first end 49 of spring 47. Anchor 53 includes a substantially flat top surface 55 and a substantially flat bottom surface 57. Anchor 53 is additionally shaped to define a pair of spaced apart slots 59-1 and 59-2, each slot 59 extending transversely through anchor 53 from top surface 55 to bottom surface 57. Each slot 59 is sized and shaped to fittingly receive an associated tab 45 from base 13. In this manner, anchor 53 is designed to be fixedly secured onto base 13.

A plurality of stepped surfaces 61-1, 61-2, 61-3 and 61-4 are formed onto and protrude up from top surface 55 of anchor 53. Surfaces 61 are sized and shaped to matingly engage corresponding surfaces formed in cover 21, thereby further securing anchor 53 fixed in place.

A generally U-shaped lancet support member 63 is integrally formed onto second end 51 of spring 47. As will be described further below, support member 63 is adapted for linear displacement relative to anchor 53 through the expansion and retraction of spring 47.

Support member 63 includes a rectangular platform 65 which is integrally formed onto second end 51 of spring 47. Platform 65 includes a substantially flat top surface 67 and a substantially flat bottom surface 69. A shallow recess 71 is formed into top surface 67 and is sized and shaped to fittingly receive lancet 17, as will be described further below. Recess 71 is shaped so as to define a pair of posts 73 which are sized and shaped to penetrate through corresponding holes in lancet 17.

Support member 63 additionally includes a pair of arms 75-1 and 75-2 formed onto opposite sides of support member 63 and which extend rearwardly in parallel with one another. Each arm 75 is in the form of an elongated block which is uniformly rectangular in lateral cross-section along its length and which includes a flat abutment surface 77 against which a hammer (or other similar striking device) in the compatible analyte test monitor can strike in order to perform the lancing operation, as will be described further below.

Lancet carrier 15 is mounted on base 13 with anchor 53 fixedly secured to base 13 and with support member 63 free to slide linearly on base 13. Specifically, anchor 53 is disposed so that tabs 45 on base 13 fittingly project through slots 59 in anchor 53. In this manner, anchor 53 is fixed in place in relation to base 13.

Having secured anchor 53 to base 13, each arm 75 lies within a corresponding recess 43 in base 13 and bottom surface 69 of platform 65 lies in direct contact against top surface 23 of base 13. Due to the construction of spring 47, the application of a forward force onto abutment surfaces 77 causes platform 65 (and, in turn, lancet 17 mounted thereon) to slide along top surface 23 in the forward direction. Upon the removal of said forward force, the resilient nature of spring 47 retracts platform 65 in the rear direction and back to its original position.

Lancet 17 is a unitary member which is designed to be mounted on lancet carrier 15. Lancet 17 is preferably constructed from a single sheet of metal which is shaped through a stamping or etching process. However, it is to be understood that lancet 17 could be manufactured out of alternative materials (e.g., plastics) and/or formed using alternative construction processes (e.g., molding or grinding processes) without departing from the spirit of the present invention.

Lancet 17 comprises a substantially flat bow-shaped tab 79 which is shaped to include a pair of circular holes 81. A sharpened needle 83 is integrally formed onto and projects orthogonally out from the front edge of tab 79. Needle 83 is sized and shaped to pierce the skin of a patient in order to produce a blood sample. Needle 83 is represented herein as having a flattened shape with a single sharpened tip. However, it is to be understood that needle 83 is not limited to any one particular construction. Rather, it is to be understood that needle 83 could be modified (e.g., to include multiple tips or to have a cylindrical shape) without departing from the spirit of the present invention.

Lancet 17 is designed to be mounted on top surface 67 of platform 65. Specifically, bow-shaped tab 79 is sized and shaped to fit snugly within recess 71 in platform 65, with posts 73 fittingly projecting through holes 81 in order to secure tab 79 in place on platform 65. Accordingly, with tab 79 mounted on platform 65 as described above, needle 83 of lancet 17 extends orthogonally forward from the front edge of platform 65. In this manner, the forward displacement of U-shaped lancet support member 63 along top surface 23 of base 13 ultimately causes the sharpened tip of needle 83 to penetrate out past front walls 31 and into the skin of the patient, as will be described further below.

It should be noted that constructing lancet 17 as a separate component from lancet carrier 15 provides a notable advantage. Specifically, because lancet 17 is constructed separately from lancet carrier 15, modifications to the particular geometry of needle 83 can be made simply by manufacturing alternative types of lancets 17. As long as any alternative design to lancet 17 includes tab 79 (thereby enabling said lancet to be mounted onto platform 65), said lancet can be utilized in analyte test device 11 in place of lancet 17. In this manner, the manufacturer can readily modify the geometry of needle 83 by replacing lancet 17 with an alternative lancet but without requiring the manufacturer to redesign lancet carrier 15, which is highly desirable.

Analyte test strip 19 is preferably in the form of an electrochemical test strip which is constructed to measure the concentration of a particular analyte, such as glucose, in a blood sample applied thereto. Test strip 19 is preferably constructed as a thin, rectangular member which includes a top surface 85, a bottom surface 87, a first end 89 and a second end 91.

Test strip 19 preferably includes a non-conductive substrate 93 and at least a pair of carbon-layer electrodes 95-1 and 95-2 which are deposited onto substrate 93 along a portion of its length in a spaced-apart relationship, electrode 95-1 serving as the reference electrode for test strip 19 and electrode 95-2 serving as the working electrode for test strip 19. An optional third electrode 95-3 may be provided which serves as the trigger electrode for test strip 19 (i.e., an electrode which measures whether an adequate blood sample has been deposited on test strip 19). Together, electrodes 95 define a reaction area (not shown) proximate first end 89. An enzyme (not shown) which produces an electrical reaction when exposed to a particular analyte (e.g., glucose) is applied to working electrode 95-2 within the reaction area. In addition, a fill area 97 is provided along first end 89 and is in fluid communication with the reaction area (e.g., by means of a capillary tube or some type of conventional wicking element).

In order to measure the concentration of a particular analyte in a patient's blood, the patient is required to deposit a blood sample onto fill area 97 of test strap 19. The blood sample, in turn, is wicked and deposited deposited across electrodes 95 in the reaction area. Simultaneously, a voltage provided by the compatible analyte test monitor is applied across electrodes 95 at second end 91, thereby effectively creating a closed circuit. The application of the blood sample on the enzyme deposited on working electrode 95-2 creates an electrical reaction. In response to said reaction, a current (commonly referred to in the art as the working current) is produced which travels along working electrode 95-2, the value of said working current being directly related to the concentration of the particular analyte in the blood sample. Accordingly, with device 11 properly loaded into the compatible analyte test meter, the meter is capable of measuring the value of the working current along working electrode 95-2 and, in turn, using said value to calculate the analyte concentration in the blood sample (e.g., by multiplying said value by a scaling factor).

It should be noted that the present invention is not limited to the particular construction of test strip 19. Rather, it is to be understood that test strip 19 could be replaced with alternative types of conventional analyte test strips without departing from the spirit of the present invention.

Test strip 19 is press-fit mounted onto the underside of cover 21. As will be described further below, the length of test strip 19 is such that first end 89 is disposed in direct contact against the skin of the patient (and in close proximity to the wound site created using lancet 17) when the patient disposes his/her finger against skin receiving surface 35 in base 13. In this manner, a blood sample generated using lancet 17 is directed onto test strip 19, which is highly desirable.

As seen most clearly in FIG. 1, cover 21 is secured to base 13 over lancet carrier 15, lancet 17 and test strip 19 to create a unitary, substantially enclosed, disposable test cartridge with both lancing and analyte measurement capabilities. Cover 21 is preferably in the form of a unitary member which is constructed out of rigid and durable plastic material using conventional molding techniques. As will be described further below, cover 21 is press-fit mounted onto base 13 and may be further secured thereto by means of ultrasonic welding or other suitable securement means (e.g., an adhesive).

Figure 3:
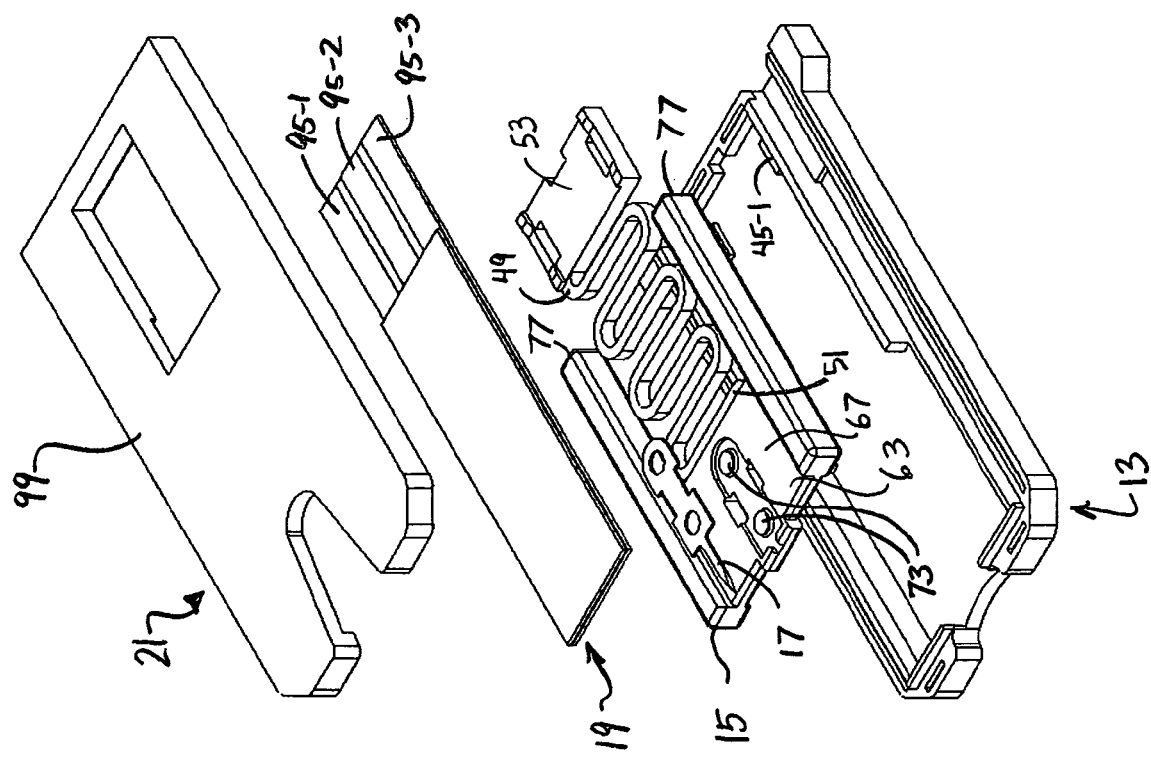
FIG. 3 is a top, front, right side, exploded perspective view of the device shown in FIG. 1.

As seen most clearly in FIGS. 3-5, cover 21 includes a substantially flat top surface 99 and a substantially flat bottom surface 101. A pair of elongated sidewalls 103-1 and 103-2 extends orthogonally downward from bottom surface 101 and are positioned along the length of the right and left side edges, respectively, of cover 21. A longitudinal rib 105 is formed onto the bottom surface of each sidewall 103, each rib 105 being sized and shaped to fittingly protrude into an associated groove 29 in sidewalls 27 so as to facilitate in the retention of cover 21 on base 13.

A pair of spaced apart front walls 107-1 and 107-2 extend orthogonally downward from bottom surface 101 and a positioned along the front edge of cover 21. A shortened rib 109 is formed onto the bottom surface of each front wall 107, each rib 109 being sized and shaped to fittingly protrude into an associated groove 33 in front walls 31 so as to facilitate in the retention of cover 21 on base 13. A notch 111 is formed into the rear surface of each front wall 107 and serves, in part, to retain test strip 19 in securement against bottom surface 101 of cover 21, as will be described further below.

Cover 21 is additionally shaped to define a generally U-shaped opening 113 along its front edge in between front walls 107-1 and 107-2. Opening 113 is provided in cover 21 in order to render fill area 97 of test strip 19 externally visible to the user. In this manner, the user is able to visually inspect whether an adequate blood sample has been applied to the fill area 97 during its use, which is highly desirable.

A shortened rear wall 115 extends orthogonally downward from bottom surface 101 and is positioned along a portion the rear edge of cover 21. A pair of shortened ribs 117 are formed onto the bottom surface of rear wall 115, each rib 117 being sized and shaped to fittingly protrude into an associated groove 39 in rear wall 37 to facilitate in the retention of cover 21 on base 13.

Figure 2:
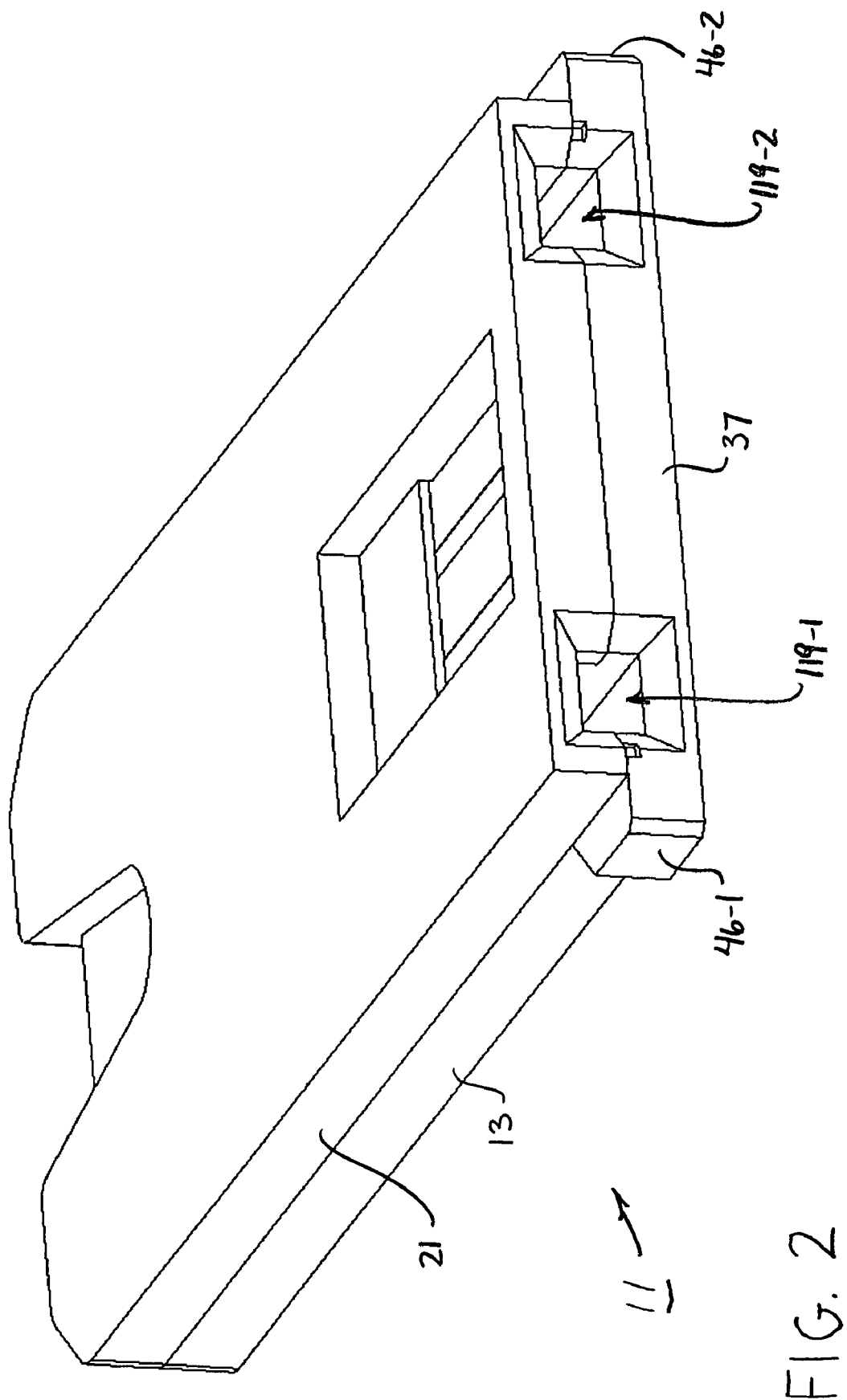
FIG. 2 is a top, rear, right side perspective view of the device shown in FIG. 1.

It should be noted that, with device 11 configured in its assembled form, base 13 and cover 21 together define a pair of openings 119-1 and 119-2 along their common rear surfaces, as seen most clearly in FIG. 2. Each opening 119 is generally square shaped in lateral cross-section and is minimized in size to reduce the risk of contamination within device 11. As will be described further below, each opening 119 serves as a path through which an actuation device (e.g., a hammer) within the compatible analyte test monitor can penetrate so as to urge lancet support member 63 (and, in turn, lancet 17) forward.

A pair of longitudinal recesses 121 is formed into bottom surface 101 of cover 21 and is disposed in direct alignment above recesses 43 in base 13 when device 11 is disposed in its assembled form. Each recess 121 is sized and shaped to fittingly receive the top surface of an associated arm 75 and thereby assist in limiting lancet support member 63 to linear displacement.

A pair of trapezoidal projections 123 is formed onto and protrude downwardly from bottom surface 101 of cover 21. Each projection 123 includes a plurality of steps, or ratchets, which are sized and shaped to matingly engage stepped surfaces 61 on anchor 53 in order to secure anchor 53 in a fixed position within device 11.

Analyte test strip 19 is adapted to be retained against the underside of cover 21. Specifically, top surface 85 of test strip 19 is disposed against bottom surface 101 of cover 21, with first end 89 of test strip 19 wedged against the rear surface of front walls 107 and second end 91 of test strip 19 wedged against the front surface of rear wall 115. With test strip 19 mounted on cover 21 in this manner, electrodes 95 at second end 91 of test strip 19 are externally accessible through a rectangular window 125 in cover 21. Accordingly, with test strip 19 properly installed into a compatible monitor, a conductive element (e.g., a metal clip) from the monitor can project through window 125 in cover 21 and directly contact electrodes 95, thereby establishing an electrical path between test strip 19 and the monitor. As such, working current present on working electrode 95-2 can be readily measured by the monitor, which is highly desirable.

It should further be noted that test strip 19 may be constructed to include calibration information directly thereon, said calibration information being stored in any conventional medium (e.g., as a barcode, read-only memory (ROM), one or more resistors, a particular pattern of interconnected conductive pads or a colored window) which can be easily read by the monitor when test strip 19 is properly loaded.

Figure 6:
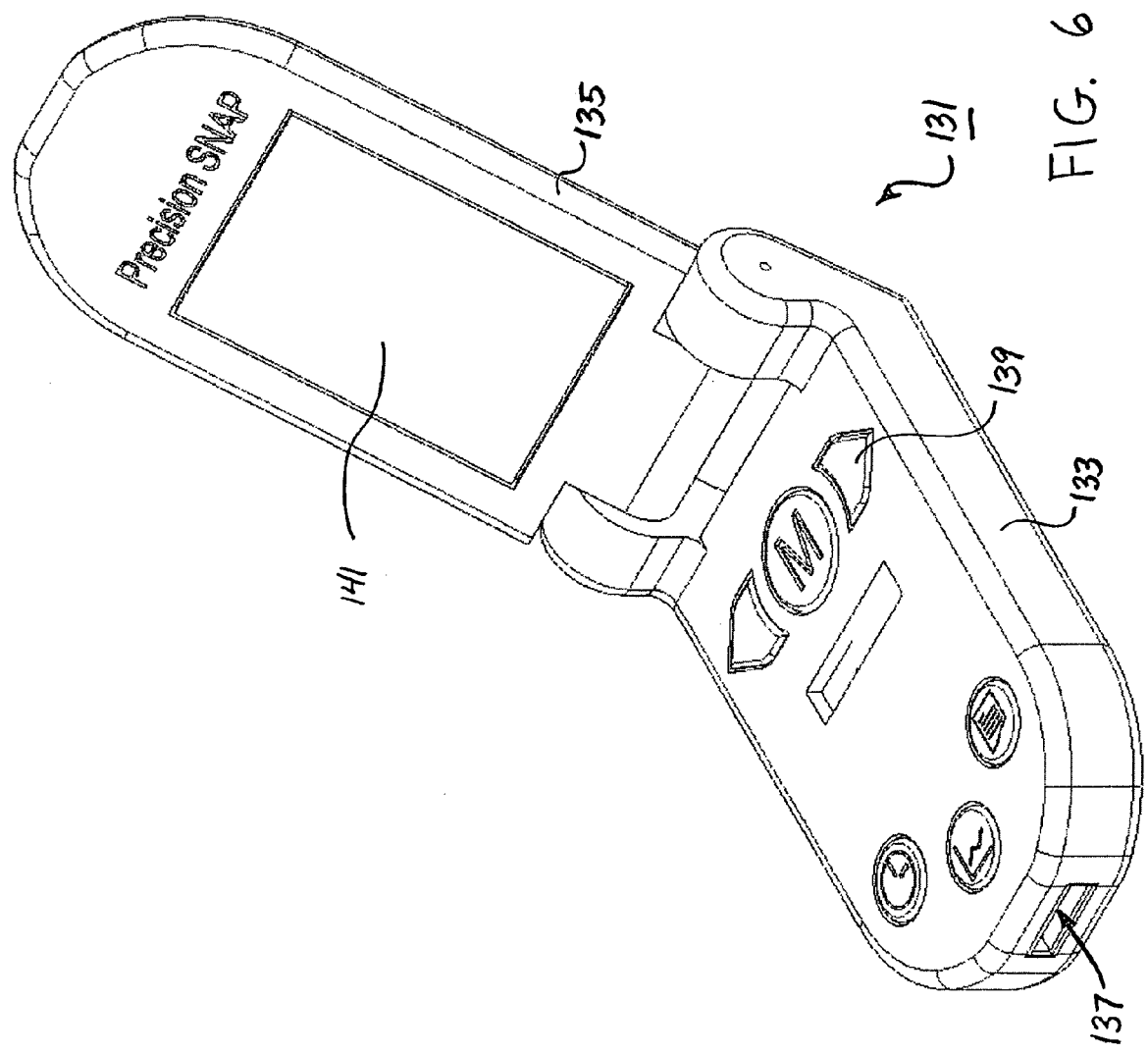
FIG. 6 is a top, front, right side exploded view of a blood glucose meter designed specifically for use in conjunction with the device shown in FIG. 1.
Figure 7:
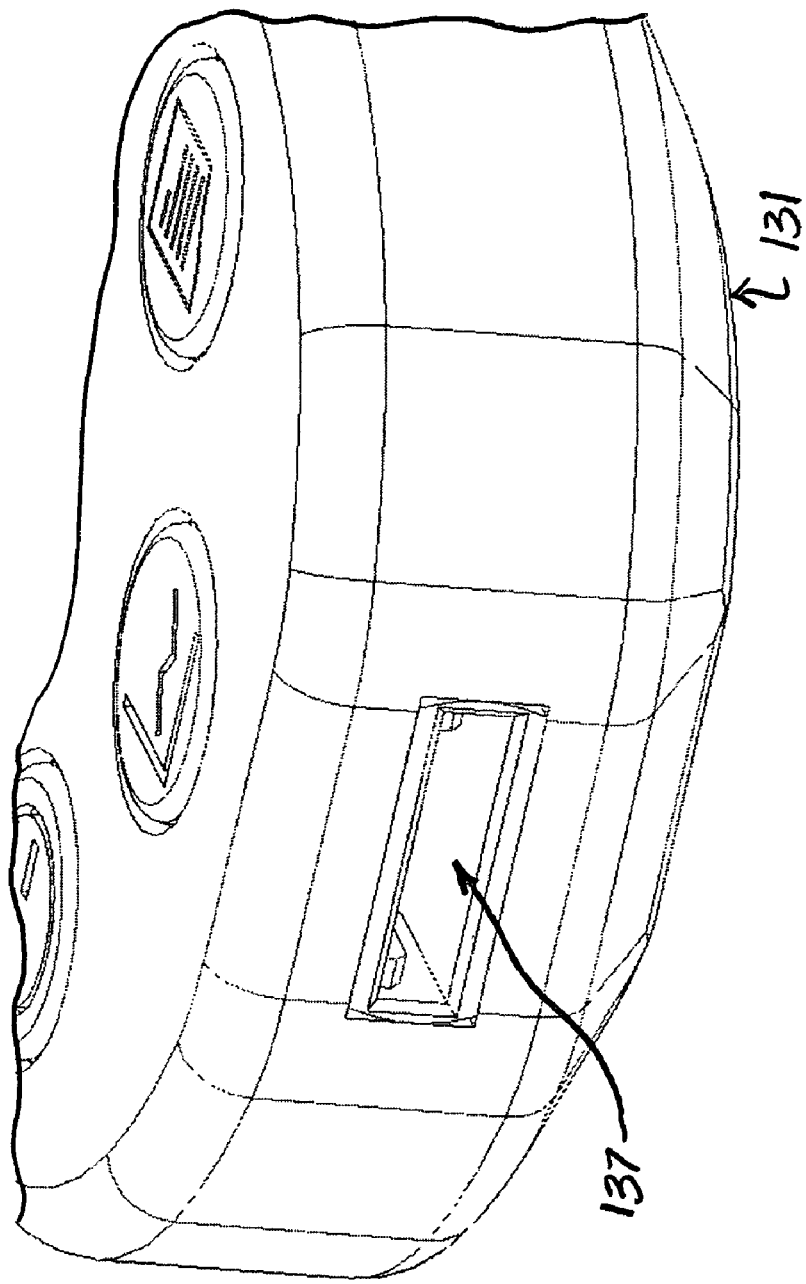
FIG. 7 is an enlarged, fragmentary, top, front, right side view of the blood glucose meter shown in FIG. 6.

Referring now to FIG. 6, there is shown a blood glucose meter 131 which is designed specifically for use in conjunction with device 11. Meter 131 includes a base 133 and a cover 135 pivotally mounted onto base 133. Base 133 is provided with a test strip port 137 which is sized and shaped to matingly receive device 11. Base 133 is also provided with one or more externally accessible buttons 139 for controlling the operation of meter 131. A screen 141 is provided on cover 135 as a means for visually displaying blood glucose results calculated by meter 131.

As seen most clearly in FIG. 6, port 137 has a keyed-type lateral cross-section which matches the lateral cross-section of device 11. In this manner, the particular shape of port 137 serves (1) to ensure the installation of device 11 into meter 131 in the proper orientation and (2) to enable meter 131 to engage wings 46 of device 11 when inserted thereinto, thereby precluding the inadvertent removal of device 11 from meter 131 (e.g., when meter 131 is tilted forward).

It should be noted that meter 131 represents one type of blood glucose monitor which is designed to operate in conjunction with device 11. However, it is to be understood that alternative types of meters compatible with device 11 could be provided without departing from the spirit of the present invention.

Configured in its assembled form, device 11 can be used in the following manner to acquire a blood sample and, in turn, analyze the concentration of a particular analyte in said blood sample. First, an individual analyte test device 11 is removed from its protective wrapping. Once unpackaged, device 11 is loaded by the patient into the appropriate test port of a compatible analyte test monitor. It should be noted that penetrable seals may additionally be provided for device 11 (e.g., over openings 119 or across front walls 31) in order to further shield device 11 from contamination prior to its use.

With device 11 properly installed into a compatible test monitor, conductive leads in the monitor project through window 125 and are disposed in electrical contact against electrodes 95, thereby establishing a current path between test strip 19 of device 11 and the central processing unit (CPU) of the monitor.

In order to perform an blood test, the patient is required to dispose the desired test site (e.g., the patient's finger) against first end 89 of test strip 19 as well as against front walls 31 of base 13. As can be appreciated, when adequate pressure is applied against front walls 31, the steep inward contour of skin receiving surface 35 serves to distend and bulge the patient's skin, thereby causing the patient's imminent wound site to be replete with blood. With the patient's skin disposed against device 11 in this manner, the firing mechanism for the monitor is activated (e.g., by depressing a button on the monitor or as a result of the application of pressure along the front end of device 11 which exceeds a predetermined threshold).

Activation of the firing mechanism causes a two-pronged hammer or other similar device present in the monitor to project through openings 119 in device and contact abutment surfaces 77 of lancet support member 63. The force of the firing mechanism would, in turn, displace lancet support member 63 linearly forward until the sharpened tip of needle 83 penetrates into the patient's skin. Lancet support member 63 advances forward until it strikes against raised abutment surfaces 34 in base, thereby limiting further forward advancement.

Immediately thereafter, the monitor retracts its firing mechanism out from device 11. Upon the withdrawal of the forward force onto arms 75 by the firing mechanism, the resilient nature of spring 47 similarly draws lancet support member 75 rearward to its original position (with the sharpened tip of needle 83 fully retracted to preclude against further skin pricks).

Upon lancing the patient's skin, blood from the wound site is deposited onto fill area 97 of strip 19, with U-shaped opening 113 enabling the patient to visibly inspect whether an adequate blood sample has been supplied onto strip 19 in order to perform an assay. Once an adequate blood sample has reached the reaction area of test strip 19 (i.e., activating trigger electrode 95-3), the monitor then measures the working current present along working electrode 95-2 (the working current resulting from the reaction between the enzyme present on electrode 95-2 and the blood sample applied thereto). Once the monitor measures the working current, the CPU calculates the concentration of the analyte in the blood sample using the working current (e.g., by multiplying the working current by a known scaling factor). The results of said calculation are preferably shown on a digital display on the monitor.

Upon completion of the assay, the individual device 11 is removed from the monitor and, in a subsequent step, is discarded. In this manner, it is to be understood that device 11 is designed as a single-use, disposable cartridge. Any additional testing can be performed in the same manner as described above using additional cartridges 11.

It should be noted that numerous modifications could be made to device 11 without departing from the spirit of the present invention. For example, it is to be understood that selected components of device 11 could be modified and/or arranged in an alternative configuration without departing from the spirit of the present invention, as will be described further in detail below.

Figure 8:
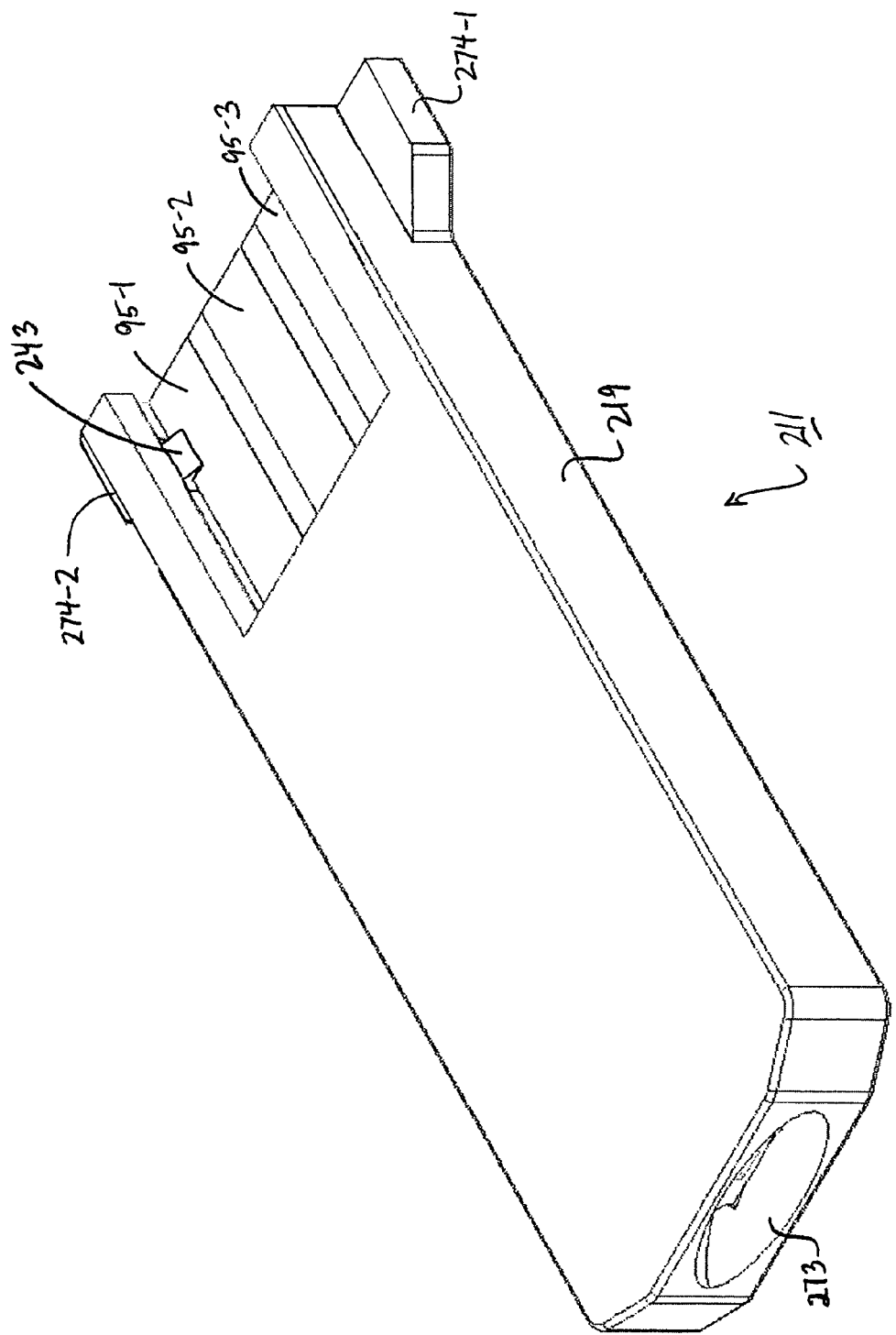
FIG. 8 is a top, front, right side perspective view of a second embodiment of an analyte test device which is constructed according to the teachings of the present invention.
Figure 9:
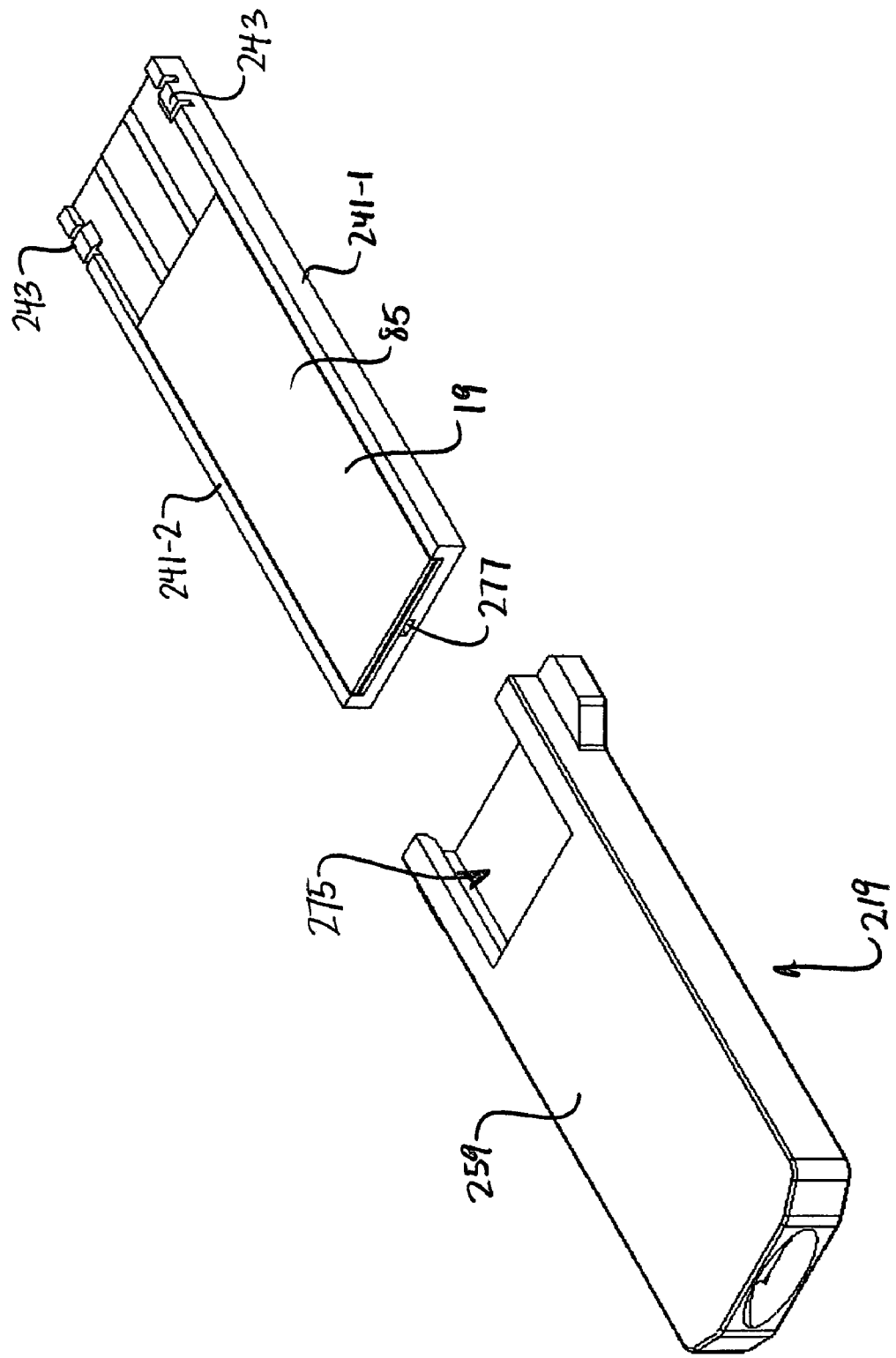
FIG. 9 is a top, front, right side, partially exploded perspective view of the device shown in FIG. 8.
Figure 10:
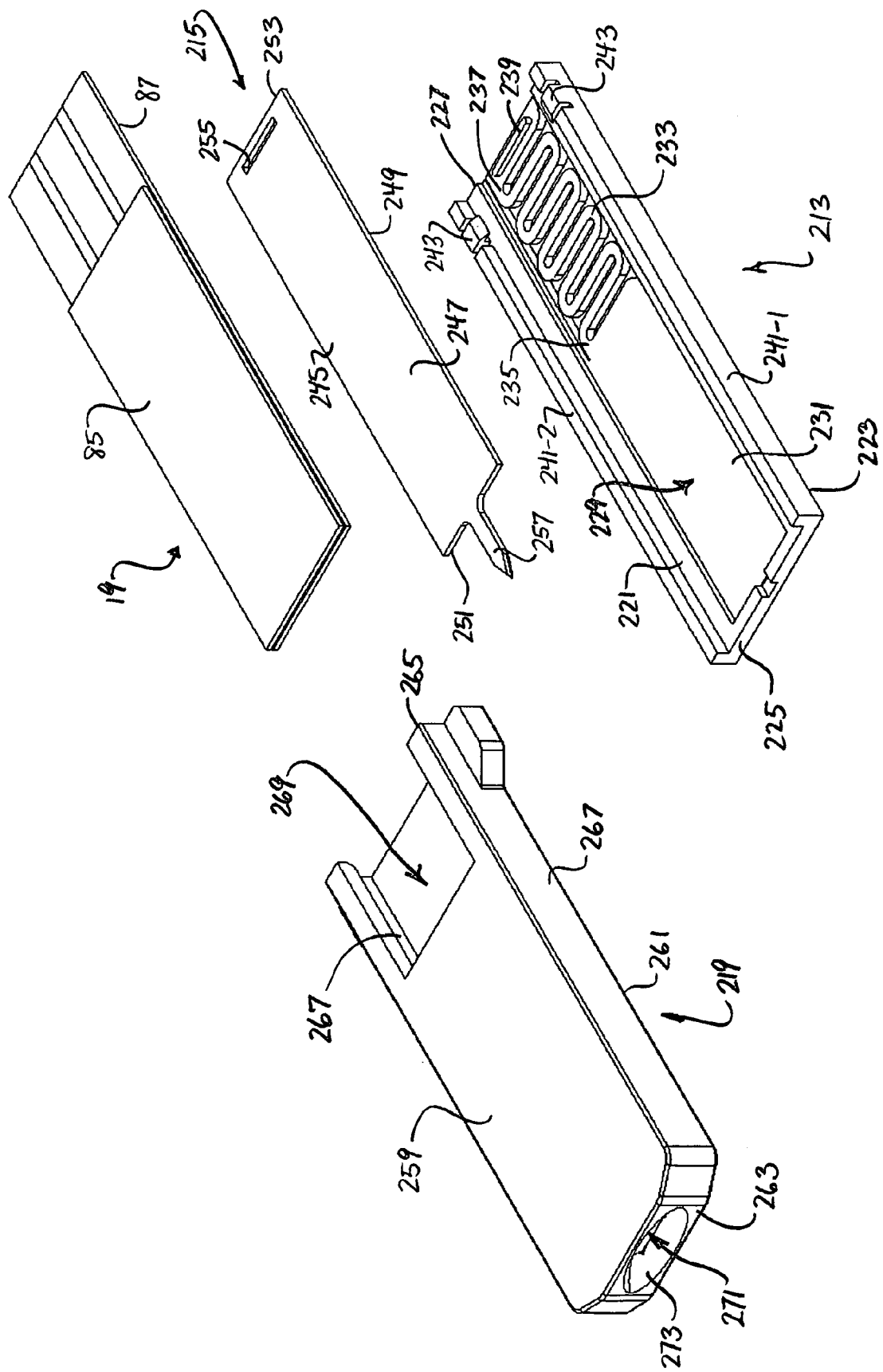
FIG. 10 is a top, front, right side, fully exploded perspective view of the device shown in FIG. 8.
Figure 11:
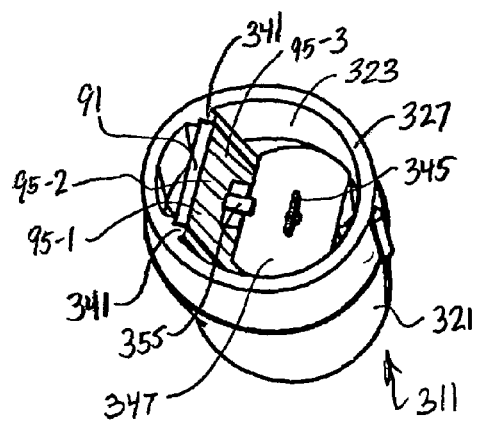
FIG. 11 is a top, front perspective view of a third embodiment of an analyte test device which is constructed according to the teachings of the present invention.
Figure 12:
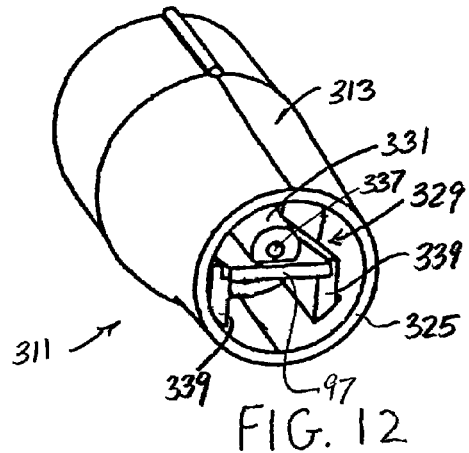
FIG. 12 is a bottom, right side perspective view of the device shown in FIG. 11.
Figure 13:
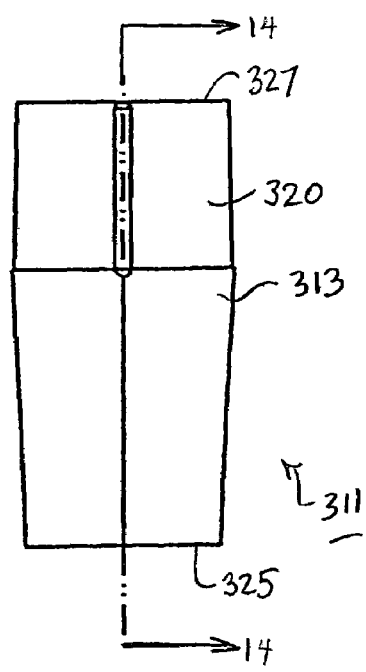
FIG. 13 is a right plan view of the device shown in FIG. 11.
Figure 14:
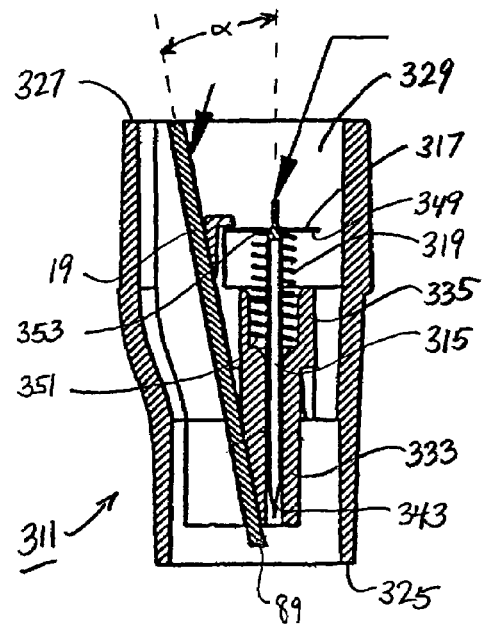
FIG. 14 is a section view of the device shown in FIG. 13 taken along lines 14-14.

Specifically, referring now to FIGS. 8-10, there is shown a second embodiment of an analyte test device which is constructed according to the teachings of the present invention, the device being identified generally by reference numeral 211. Device 211 is similar to device 11 in that device 211 is constructed as a unitary, single-use, integrated disposable test cartridge which has a substantially low profile and flat design and which has roughly the same dimensions as device 11.

Device 211 comprises a base 213, a lancet 215 fixedly mounted onto base 213, an analyte test strip 19 mounted on base 213 over lancet 215, and a protective housing 219 which is adapted to receive and substantially enclose base 213, lancet 215 and test strip 19, as will be described further below. Preferably, device 211 can be mass produced with each individual device 211 enclosed within a hermetically-sealed package to protect against contamination, humidity and inadvertent lancing.

Base 213 is a unitary member which is preferably constructed of a rigid and durable plastic material using conventional molding techniques. Base 213 includes a top surface 221, a substantially flat bottom surface 223, a front end 225 and a rear end 227.

A shallow recess 229 is formed into top surface 221 so as to define a lancet support surface 231 which lies slightly beneath top surface 221, lancet support surface 231 extending nearly the entirely length of base 213. A spring 233 is integrally formed into lancet support surface 231 proximate rear end 227, spring 233 comprising a first end 235 and a second end 237. A laterally-extending rib 239 is integrally formed onto and projects orthogonally up from second end 237 of spring 233, the top surface of rib 239 being in the same plane as top surface 221.

In addition, a pair of elongated sidewalls 241-1 and 241-2 extends orthogonally upward from top surface 221 and are positioned along the length of the right and left side edges, respectively, of base 213. A small, pivotable finger 243 is formed into each sidewall 241 proximate rear end 227.

Lancet 215 is an elongated, flat and unitary member which is preferably constructed from a single sheet of metal which is subsequently shaped through one or more stamping operations. However, it is to be understood that lancet 215 could be manufactured out of alternative materials (e.g., plastics) and/or formed using alternative construction processes (e.g., molding processes) without departing from the spirit of the present invention.

Lancet 215 comprises an elongated, thin rectangular member 245 which includes a flat top surface 247, a flat bottom surface 249, a front end 251 and a rear end 253. Member 245 is shaped to include a transverse slot 255 along rear end 253 which is sized and shaped to fittingly receive rib 239. In this manner, lancet 215 can be fixedly mounted onto base 213 by disposing member 245 within recess 229 such that rib 239 fittingly protrudes through slot 255. With lancet 215 mounted on base 213 in this manner, it should be noted that top surface 247 of lancet 215 lies substantially flush with top surface 221 of base 213.

Lancet 215 additionally includes a flat, sharpened needle 257 which is integrally formed onto and projects orthogonally out from the front end 251 of member 245. Needle 257 is sized and shaped to pierce the skin of a patient in order to produce a blood sample and is represented herein as having a flattened shape with a single sharpened tip. However, it is to be understood that needle 257 is not limited to any one particular construction. Rather, it is to be understood that needle 257 could be modified (e.g., to include multiple tips or to have a cylindrical shape) without departing from the spirit of the present invention.

Analyte test strip 19 is preferably mounted on base 213 over lancet 215 such that its bottom surface 87 lies flat on top surface 221 and such that its top surface 85 lies flush with the top surface of sidewalls 241, as seen most clearly in FIG. 9. It should be noted that with lancet 215 and test strip 19 mounted on base 13 as described above, fingers 243 in sidewalls 241 engage test strip 19 to retain the components together.

Housing 219 is a unitary member which is preferably constructed of a rigid and durable plastic material using conventional molding techniques. Housing 219 is represented herein as being in the form of a substantially enclosed cap which includes a flat top surface 259, a flat bottom surface 261, a front end 263, a substantially open rear end 265 and a pair of sidewalls 267 which together define a substantially enclosed interior cavity 269. An opening 271 is formed in front end 263 and is in communication with interior cavity 269. An inwardly contoured skin receiving surface 273 is formed into front end 263 immediately surrounding opening 271 and serves to facilitate in drawing blood to the area in the patient's skin which is to be lanced using lancet 215.

In addition, a pair of outwardly extending wings 274-1 and 274-2 are formed onto sidewalls 241-1 and 241-2, respectively, along the rear of base 213. Wings 274 serve two principal functions: (1) to provide device 211 with a keyed-type lateral cross-section along its rear end, thereby ensuring the installation of device 211 within a compatible blood glucose monitor in the proper orientation, and (2) to ensure that device 211 is suitably retained (i.e., locked) within the compatible blood glucose monitor when installed therein.

With lancet 215 and test strip 19 mounted on base 213 in the manner described above, the unitary piece resulting therefrom is slid into interior cavity 269 through open rear end 265. A window 275 is formed in top surface 259 at rear end 265 so as to render electrodes 95 externally accessible, as shown in FIG. 8.

Device 211 can be used in the following manner to acquire a blood sample and, in turn, analyze the concentration of a particular analyte in said blood sample. First, an individual analyte test device 211 (in its assembled form) is removed from its protective wrapping. Once unpackaged, device 211 is loaded by the patient into the appropriate test port of a compatible analyte test monitor. It should be noted that penetrable seals may additionally be provided for device 211 (e.g., over front end 263) in order to further shield device 211 from contamination prior to its use.

With device 211 properly installed into a compatible test monitor, conductive leads in the monitor project through window 275 and are disposed in electrical contact against electrodes 95, thereby establishing a current path between test strip 19 of device 211 and the central processing unit (CPU) of the monitor.

In order to perform an blood test, the patient is required to dispose the desired test site (e.g., the patient's finger) against front end 263 of housing 219. As can be appreciated, when adequate pressure is applied against front end 263, the steep inward contour of skin receiving surface 273 serves to distend and bulge the patient's skin, thereby causing the patient's imminent wound site to be replete with blood. With the patient's skin disposed against device 211 in this manner, the firing mechanism for the monitor is activated (e.g., by depressing a button on the monitor or as a result of the application of pressure along the front end 263 of device 211 which exceeds a predetermined threshold).

Activation of the firing mechanism causes a hammer or other similar device present in the monitor to project through open rear end 265 of housing 219 and contact rear end 227 of base 213. The force of the firing mechanism causes second end 237 of spring 233 to advance forward towards first end 235 (thereby compressing spring 233) which, in turn, advances lancet 215 forward. The forward advancement of lancet 215 causes the sharpened tip of needle 257 to penetrate through a small opening 277 in front end 225 of base 213, out through opening 271 in housing 219 and, in turn, into the patient's skin.

Immediately thereafter, the monitor retracts its firing mechanism out from device 211. Upon the withdrawal of the firing mechanism, the resilient nature of spring 233 draws lancet 215 rearward to its original position (with the sharpened tip of needle 257 fully retracted back into interior cavity 269 to preclude against further skin pricks).

Upon lancing the patient's skin, blood from the wound site is deposited onto fill area 97 of strip 19. Once an adequate blood sample has reached the reaction area of test strip 19 (i.e., activating trigger electrode 95-3), the monitor then measures the working current present along working electrode 95-2 (the working current resulting from the reaction between the enzyme present on electrode 95-2 and the blood sample applied thereto). Once the monitor measures the working current, the CPU calculates the concentration of the analyte in the blood sample using the working current (e.g., by multiplying the working current by a known scaling factor). The results of said calculation are preferably shown on a digital display on the monitor.

Upon completion of the assay, the individual device 211 is removed from the monitor and, in a subsequent step, is discarded. In this manner, it is to be understood that device 211 is designed as a single-use, disposable cartridge. Any additional testing can be performed in the same manner as described above using additional cartridges 211.

Referring now to FIGS. 11-14, there is shown a third embodiment of an analyte test device which is constructed according to the teachings of the present invention, the device being identified generally by reference numeral 311. Device 311 is similar to device 11 in that device 311 is constructed as a unitary, single-use, integrated disposable test cartridge. However, device 311 differs from device 11 in that device 311 has tubular design, as will be described further below.

Device 311 comprises a housing 313, a lancet 315 slidably mounted within housing 313, a cap 317 affixed to one end of lancet 315, a spring 319 for urging cap 317 upward, and an analyte test strip 19 disposed within housing 313 in close proximity to lancet 315. Preferably, device 311 can be mass produced with each individual device 311 enclosed within a hermetically-sealed package to protect against contamination and inadvertent lancing.

Housing 313 is a unitary member which is preferably constructed of a rigid and durable plastic material using conventional molding techniques. Housing 313 has a generally tubular (i.e., cylindrical) shape and includes a sidewall 320 which comprises an outer surface 321, an inner surface 323, an open bottom end 325 and an open top end 327. The tubular shape of housing 313 serves to define a longitudinally extending interior cavity 329 which is accessible through open bottom end 325 and open top end 327, interior cavity 329 being generally circular in lateral cross-section.

A needle support 331 is integrally formed onto inner surface 323 and extends longitudinally within interior cavity 329. Needle support 331 is generally cylindrical in shape and includes a first end 333, a second end 335 and a longitudinally extending bore 337, bore 337 being of reduced diameter at first end 333 and of expanded diameter at second end 335.

A first pair of strip support members 339 is integrally formed onto inner surface 323 proximate bottom end 325. In addition, a second pair of strip support members 341 is integrally formed onto inner surface 323 proximate top end 327. Together, first and second strip support members 339 and 341 serve to retain test strip 19 in place within interior cavity 329.

It should be noted that support members 339 and 341 hold test strip 19 at an angle relative to the longitudinal axis of housing 313. Furthermore, support members 339 and 341 hold test strip 19 such that its first end 89 is spaced slightly in from bottom end 325 and such that its second end 91 is substantially co-planar with top end 327. As can be appreciated, spacing first end 89 adequately in from bottom end 325 serves to allow the patient's skin that is to be lanced to substantially distend and bulge into interior cavity 329 in order to contact first end 89. As a result, an increased supply of blood is provided in the patient's skin prior to lancing, which is highly desirable.

Lancet 315 is an elongated, cylindrical and unitary member which is preferably constructed from a single sheet of metal which is subsequently shaped through one or more stamping and/or etching operations. However, it is to be understood that lancet 315 could be formed in a different shape (e.g., to include multiple sharpened tips), manufactured out of alternative materials (e.g., plastics) and/or formed using alternative construction processes (e.g., molding processes) without departing from the spirit of the present invention.

Lancet 315 is in form of an elongated needle which includes a sharpened tip 343 at one end and a cross-bar 345 at the other end. Lancet 315 is orientated to extend axially through bore 337 in needle support 331 with sharpened tip 343 directed towards bottom end 325. In this manner, it is to be understood that first end 333 of needle support 331 serves to sufficiently stabilize (i.e., stiffen) lancet 315, which is highly desirable.

It should be noted that analyte test strip 19 and lancet 315 are disposed at an acute angle a relative to one another. As a result, first end 89 of test strip 19 is disposed in close proximity to sharpened tip 343 of lancet 315. Accordingly, once tip 343 of lancet 315 pricks the skin of a patient, the supply of blood which exits the wound site is drawn immediately onto fill area 97 of test strip 19, which is highly desirable.

A thin cap 317 is fixedly mounted onto lancet 315 and is retained in place by cross-bar 345. Cap 317 is preferably in the form of a thin disc which includes a substantially flat top surface 347 and a substantially flat bottom surface 349.

Spring 319 is mounted axially over lancet 315 and includes a first end 351 and a second end 353. First end 351 of spring 319 is retained against an annular flange formed along the interior surface of needle support 331. Second end 353 of spring 319 is disposed in contact against bottom surface 349 of cap 317. In this manner, spring 319 serves to continuously urge cap 317 and, in turn, lancet 315 upward towards top end 327. However, a fixed finger 355 provided in housing 313 serves as a stop for limiting the upward displacement of cap 317.

It should be noted that the application of a suitable downward force onto top surface 347 of cap 317 (i.e., a force greater than the compression force of spring 319) causes cap 317 and, in turn, lancet 315 to be displaced linearly downward towards bottom end 325. Upon the release of said downward force, the resilient nature of spring 319 urges cap 317 and, in turn, lancet 315 back up to its original position.

Device 311 can be used in the following manner to acquire a blood sample and, in turn, analyze the concentration of a particular analyte in said blood sample. First, an individual analyte test device 311 (in its assembled form) is removed from its protective wrapping. Once unpackaged, device 311 is loaded by the patient into the appropriate test port of a compatible analyte test monitor. It should be noted that penetrable seals may additionally be provided for device 311 (e.g., over opened top end 327 and/or over opened bottom end 325) in order to further shield device 311 from contamination prior to its use.

With device 311 properly installed into a compatible test monitor, conductive leads in the monitor project through opened top end 327 and are disposed in electrical contact against electrodes 95, thereby establishing a current path between test strip 19 of device 311 and the central processing unit (CPU) of the monitor.

In order to perform an blood test, the patient is required to dispose the desired test site (e.g., the patient's finger) against opened bottom end 325 of housing 313. As can be appreciated, when adequate pressure is applied against bottom end 325, the patient's skin bulges into interior cavity 329 and ultimately in contact against first end 89 of test strip 19. With the patient's skin disposed against device 311 in this manner, the firing mechanism for the monitor is activated (e.g., by depressing a button on the monitor or as a result of the application of pressure along the bottom end 325 of device 311 which exceeds a predetermined threshold).

Activation of the firing mechanism causes a hammer or other similar device present in the monitor to project through open top end 327 of housing 313 and abut against top surface 347 of cap 317. The force of the firing mechanism causes cap 317 and, in turn, lancet 315 to be displaced linearly in the downward direction (thereby compressing spring 319). The downward displacement of lancet 315 ultimately causes sharpened tip 343 of lancet 315 to penetrate into the patient's skin. Immediately thereafter, the monitor retracts its firing mechanism out from device 311. Upon the withdrawal of the firing mechanism, the resilient nature of spring 319 retracts lancet 315 upward to its original position.

Upon lancing the patient's skin, blood from the wound site is drawn directly into fill area 97 of strip 19. Once an adequate blood sample has reached the reaction area of test strip 19 (i.e., activating trigger electrode 95-3), the monitor then measures the working current present along working electrode 95-2 (the working current resulting from the reaction between the enzyme present on electrode 95-2 and the blood sample applied thereto). Once the monitor measures the working current, the CPU calculates the concentration of the analyte in the blood sample using the working current (e.g., by multiplying the working current by a known scaling factor). The results of said calculation are preferably shown on a digital display on the monitor.

Upon completion of the assay, the individual device 311 is removed from the monitor and, in a subsequent step, is discarded. In this manner, it is to be understood that device 311 is designed as a single-use, disposable cartridge. Any additional testing can be performed in the same manner as described above using additional cartridges 311.

Figure 15:
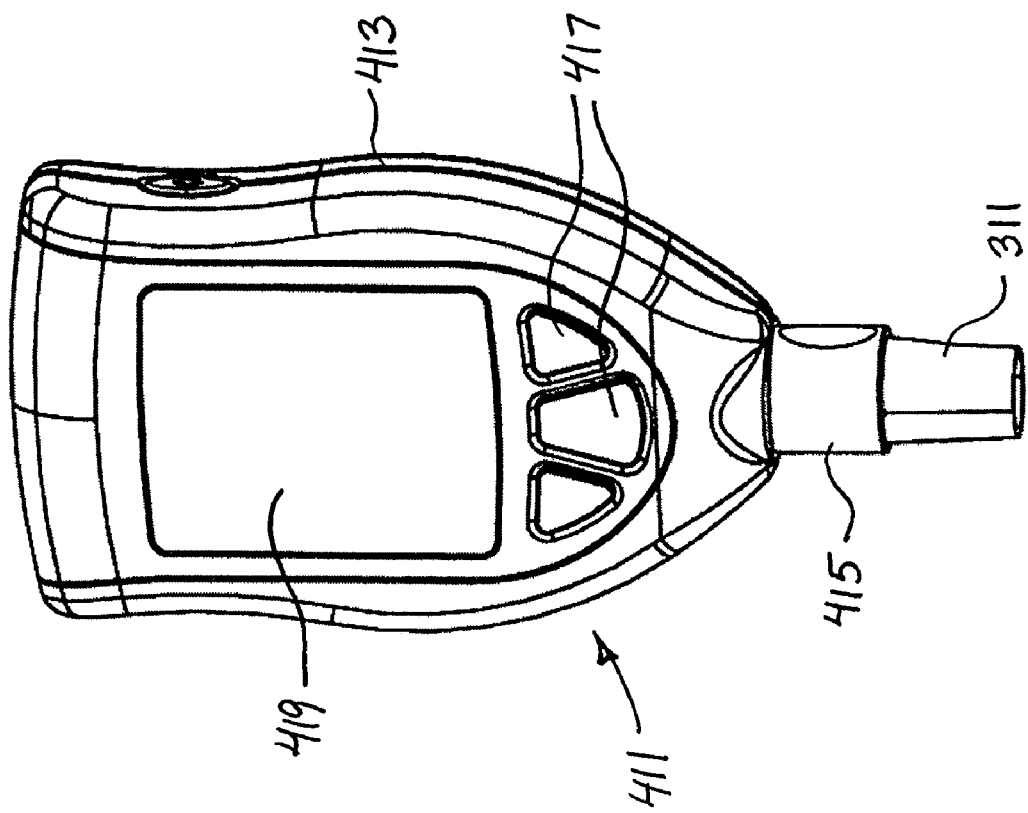
FIG. 15 is a front perspective view of a blood glucose meter designed specifically for use in conjunction with the device shown in FIG. 11.

Referring now to FIG. 15, there is shown a blood glucose meter 411 which is designed specifically for use in conjunction with device 311. Meter 411 includes a housing 413 and a tubular integrated disposable receptacle 415 which is telescopingly mounted onto one end of housing 413, receptacle 415 being sized and shaped to matingly receive device 311. It should be noted that the ability to displace receptacle 415 into housing 413 may, in turn, enable receptacle 415 to function as a trigger means for energizing and/or activating the internal firing mechanism (not shown) for device 411.

Preferably, meter 411 additionally includes one or more externally accessible buttons 417 for controlling certain operations of meter 411. An externally viewable screen 419 is also preferably provided as a means for visually displaying blood glucose results calculated by meter 411.

It should be noted that meter 411 represents one type of blood glucose monitor which is designed to operate in conjunction with device 311. However, it is to be understood that alternative types of meters compatible with device 311 could be provided without departing from the spirit of the present invention.

It should also be noted that numerous modifications could be made to device 311 without departing from the spirit of the present invention. For example, it is to be understood that selected components of device 311 could be modified and/or arranged in alternative configurations without departing from the spirit of the present invention, as will be described further in detail below.

Figure 16:
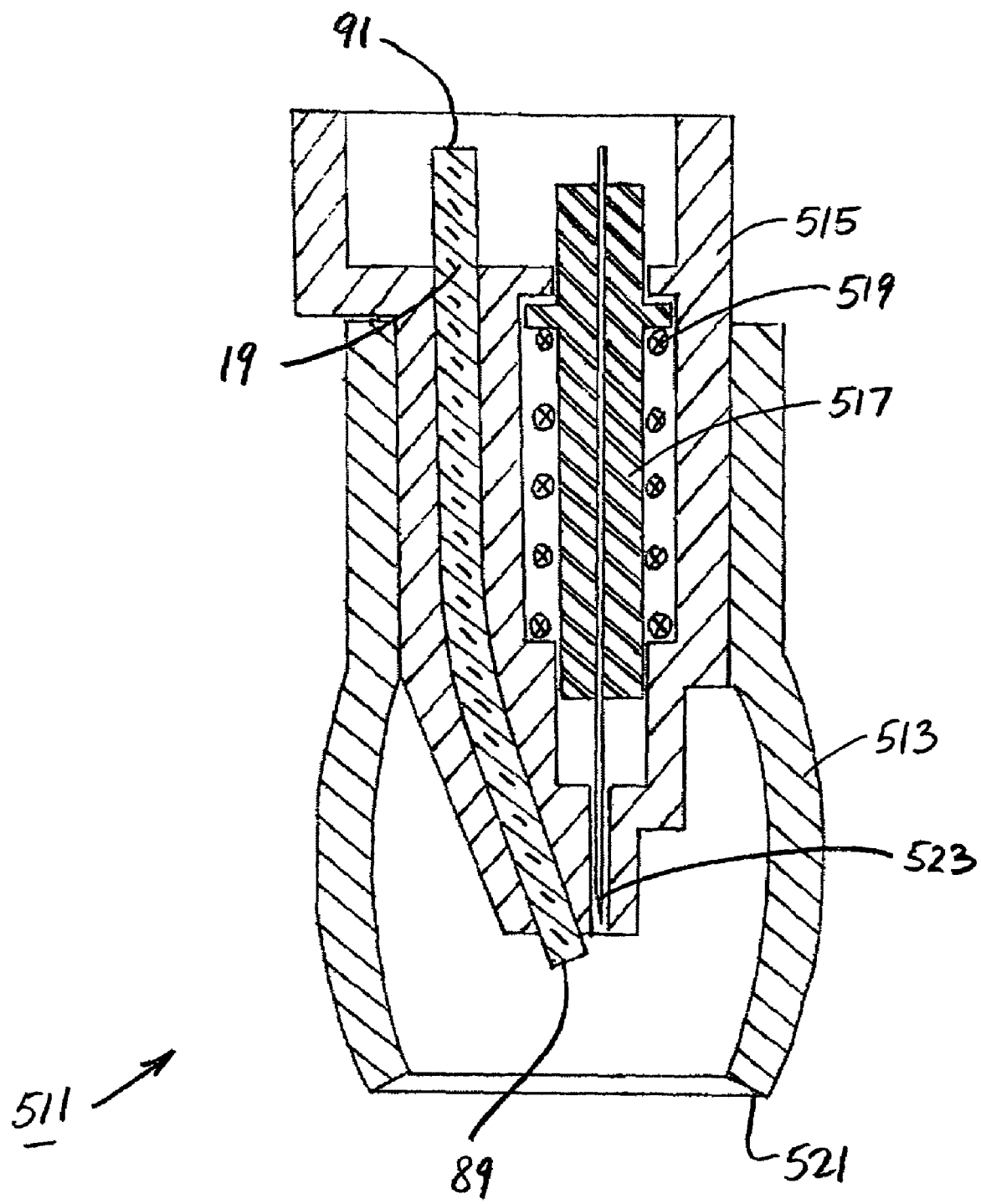
FIG. 16 is a section view of a fourth embodiment of an analyte test device which is constructed according to the teachings of the present invention.

As an example, referring now to FIG. 16, there is shown a fourth embodiment of an analyte test device which is constructed according to the teachings of the present invention, the device being identified generally by reference numeral 511. Device 511 is similar to device 311 in that device 511 is constructed as a unitary, single-use, integrated disposable test cartridge which has a generally tubular design.

Device 511 comprises a generally tubular exterior housing 513, a needle support 515 telescopingly disposed within exterior housing 513, a lancet 517 slidably mounted within needle support 515 along a substantially vertical path, a spring 519 disposed between lancet 517 and needle support 515 for urging lancet 517 upward and away from the open bottom end 521 of exterior housing 513, and an analyte test strip 19 fixedly mounted within support 515 in close proximity to lancet 517. Preferably, device 511 can be mass produced with each individual device 511 enclosed within a hermetically-sealed package to protect against contamination and inadvertent lancing.

A principal distinction between device 511 and device 311 lies in the orientation of test strip 19. Specifically, in device 511, test strip 19 is disposed such that second end 91 extends along a substantially vertical path and in parallel with the longitudinal axis of lancet 517. However, it should be noted that needle support 515 is specifically designed to bend test strip 19 about its approximate midpoint so that first end 89 of test strip 19 and the sharpened tip 523 of lancet 517 are disposed at an acute angle relative to one another, which is highly desirable for reasons enumerated above in conjunction with device 311.

Figure 17:
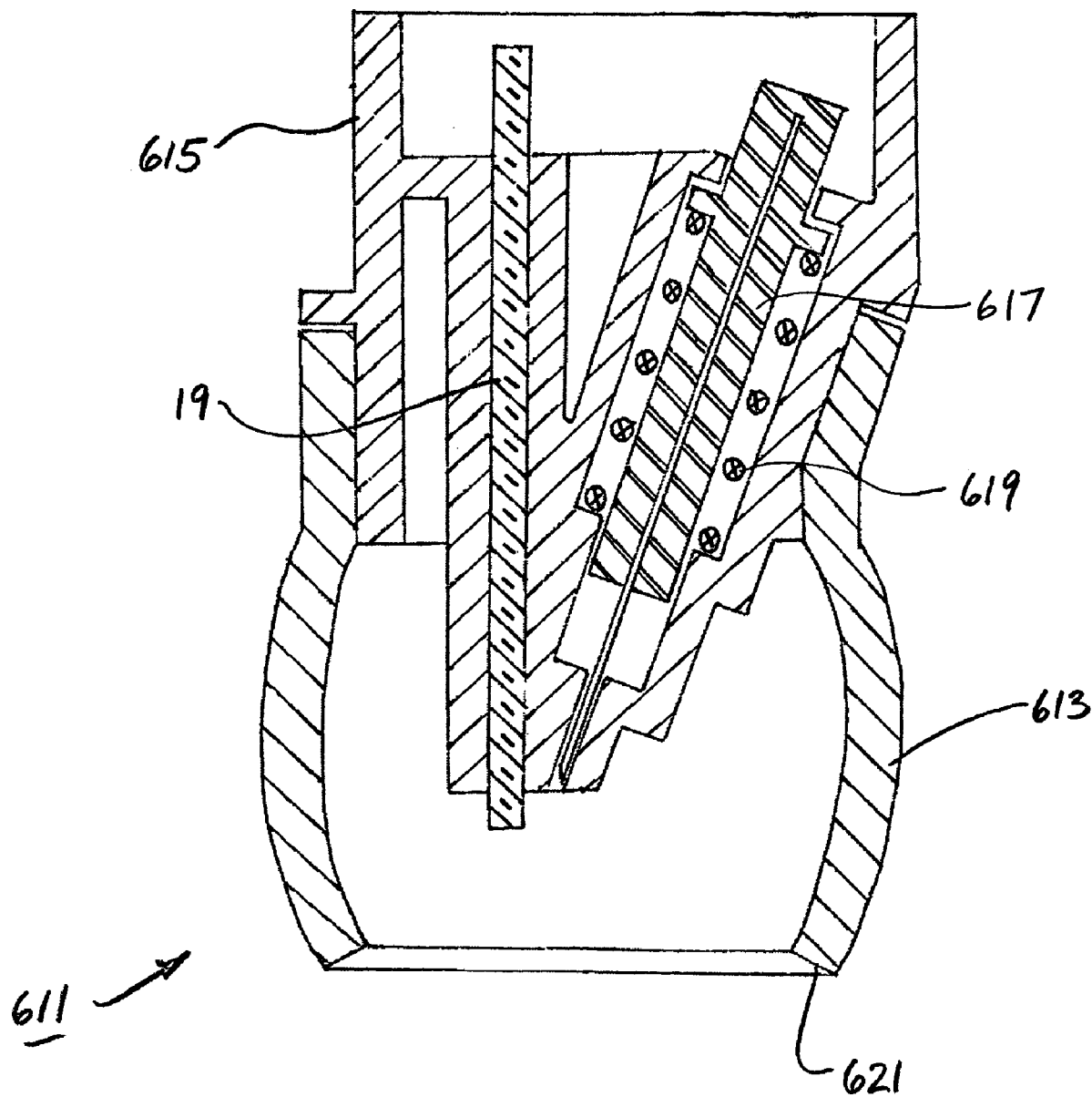
FIG. 17 is a section view of a fifth embodiment of an analyte test device which is constructed according to the teachings of the present invention.

As another example, referring now to FIG. 17, there is shown a fifth embodiment of an analyte test device which is constructed according to the teachings of the present invention, the device being identified generally by reference numeral 611. Device 611 is similar to device 311 in that device 611 is constructed as a unitary, single-use, integrated disposable test cartridge which has a generally tubular design.

Device 611 comprises a generally tubular exterior housing 613, a needle support 615 telescopingly disposed within exterior housing 613, a lancet 617 slidably mounted within needle support 615, a spring 619 disposed between lancet 617 and needle support 615 for urging lancet 617 upward and away from the open bottom end 621 of exterior housing 613, and an analyte test strip 19 fixedly mounted within support 615 in close proximity to lancet 617. Preferably, device 611 can be mass produced with each individual device 611 enclosed within a hermetically-sealed package to protect against contamination and inadvertent lancing.

A principal distinction between device 611 and device 311 lies in the orientation of each lancet and test strip 19. Specifically, in device 311, lancet 315 is disposed in a substantially vertical orientation whereas test strip 19 is disposed at an acute angle relative thereto. To the contrary, in device 611, test strip 19 is disposed in a substantially vertical orientation whereas lancet 617 is disposed at an acute angle relative thereto.

It is to be understood that various design features present in all of the above-described embodiments could be incorporated into a single cartridge which includes a plurality of individual modules, each module comprising both lancing and analytical components. As can be appreciated, such a cartridge would allow for numerous blood glucose tests to be undertaken without necessitating the unwrapping, installation and disposal of a single use cartridge after each assay.

Figure 18:
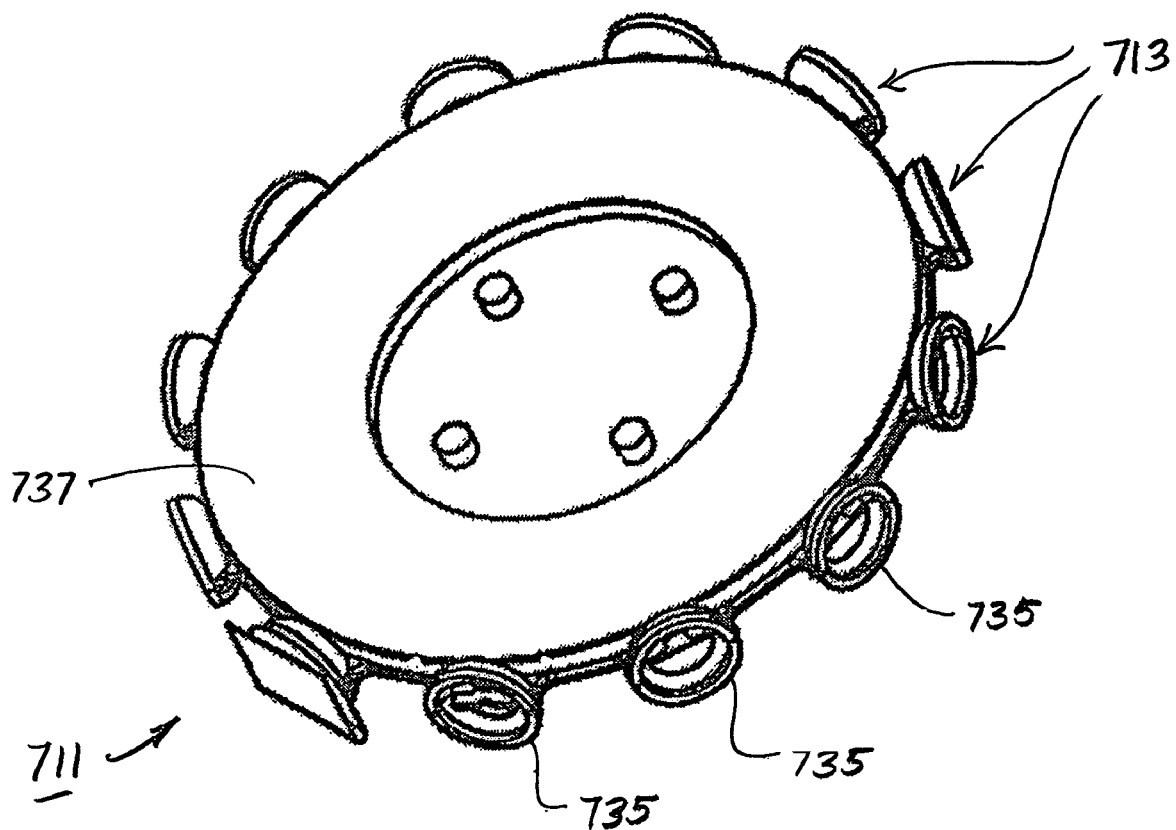
FIG. 18 is a top perspective view of a cartridge which is constructed according to the teachings of the present invention.
Figure 19:
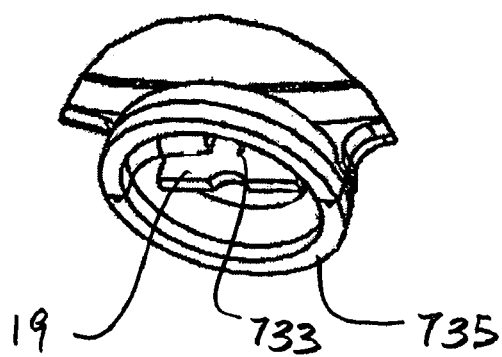
FIG. 19 is an enlarged, fragmentary perspective view of a single module in the cartridge shown in FIG. 18.
Figure 20:
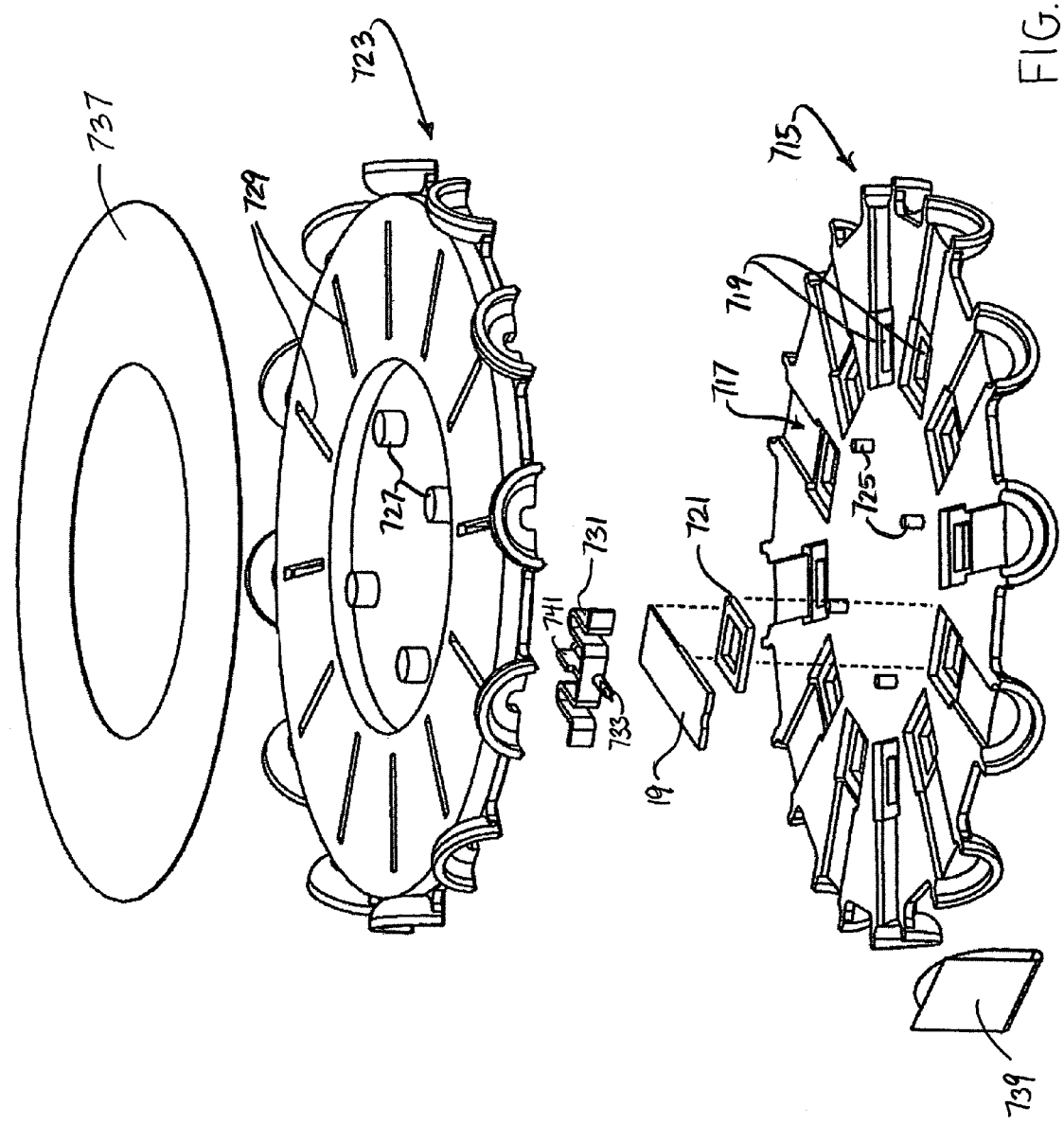
FIG. 20 is an exploded perspective view of the cartridge shown in FIG. 18.

Specifically, referring now to FIGS. 18-20, there is shown a cartridge constructed according to the teachings of the present invention, the cartridge being identified generally by reference numeral 711. Cartridge 711 includes a plurality individual test modules 713 which are radially arranged so as to provide cartridge 711 with a daisywheel-type configuration. As will be described further below, each test module 713 is individually sealed and is designed, in conjunction with a compatible analyte test meter, to lance the skin of a patient in order to draw a sample of blood and, subsequent thereto, analyze the concentration of a particular analyte in the blood sample.

Cartridge 711 includes a bottom housing 715 which is shaped to define a plurality of radially arranged recesses 717. A square-shaped opening 719 is formed within each recess 717. An analyte test strip 19 is fittingly disposed within each recess 717 in bottom housing 715, the electrodes for test strip 19 being externally accessible (i.e., for electrical contact with a compatible monitor) through its associated opening 719. Preferably, a square-shaped, adhesive seal 721 is disposed between test strip 19 and bottom housing 715 in order to protect (i.e., seal) test strip 19 from humidity or other similar outside elements which could compromise the performance of test strip 19.

A top housing 723 is fixedly mounted onto bottom housing 715 by any conventional means, such as through ultrasonic welding or using an adhesive. A plurality of alignment posts 725 formed on bottom housing 715 and a plurality of complementary bores 727 formed into top housing 723 serve to ensure the proper orientation of top housing 723 relative to bottom housing 715. A plurality of radially extending partitions (not shown) are formed onto the underside of top housing 723 and, with cartridge 711 in its assembled form, create a seal between adjacent test modules 713, which is highly desirable. In addition, top housing 723 is also shaped to include a plurality of radially extending slots 729, each slot 729 aligning directly above a corresponding test strip 19.

A W-shaped spring, or bow, 731 is fixedly secured at both of its free ends onto the underside of top housing 723, one spring 731 aligning directly above a corresponding test strip 19. A sharpened lancet 733 is fixedly mounted onto the approximate midpoint of spring 731. As such, with spring 731 secured onto top housing 723, lancet 733 is capable of being displaced radially outward by a suitable force applied thereto, spring 731 retracting lancet 733 back to its original position upon the withdrawal of said force.

With top housing 723 affixed to bottom housing 715, there are defined a plurality of pressure rings 735 (one ring 735 shown in isolation in FIG. 19). Each pressure ring 735 serves as an external passageway into a particular module 713 (i.e., through which lancet 733 can extend and lance the skin of the patient).

An annular film 737 is adhesively bonded to the top surface of top housing 723 over slots 729. Similarly, a removable flap 739 is adhesively secured over the pressure ring 735 of each module 713. Together, film 737 and flaps 739 serve to further protect (i.e., seal) each module 713 from outside elements (e.g., humidity) which could compromise the proper operation of test strip 19.

Configured in its assembled form, cartridge 711 can be used in the following manner to acquire a blood sample and, in turn, analyze the concentration of a particular analyte in said blood sample. First, cartridge 711 is removed from any protective wrapping or packaging and is loaded into the appropriate port of a compatible analyte test monitor. With cartridge 711 properly loaded, the pressure ring 735 for a single module 713 is disposed outside the monitor. It should be noted that conductive leads in the monitor project through an opening 719 and into electrical contact against the electrodes 95 of the test strip 19 for the same module 713.

In order to perform a blood test, the patient is first required to peel off the removable flap 739 which covers the exposed pressure ring 735. Next, the patient positions the desired test site (e.g., the patient's finger) against the exposed pressure ring 735, the shape of pressure ring 735 causing the test site to bulge and distend, which is highly desirable. With the patient's skin pressed against ring 735 in this manner, the firing mechanism for the monitor is activated (e.g., by depressing a button on the monitor).

Activation of the firing mechanism causes a piercing member or other similar device present in the monitor to penetrate through annular film 737 and into the slot 729 within the particular module 713. The piercing member then travels linearly outward within the path defined by slot 729 and ultimately abuts against a projection 741 formed at the approximate midpoint of spring 731. Further linear translation of the piercing member drives lancet 733 radially outward, through ring 735, and into the patient's skin.

Immediately thereafter, the monitor retracts the piercing member. Upon the retraction of the piercing member, the resilient nature of spring 731 draws lancet 733 back inside to prevent against future inadvertent skin pricks. Upon lancing the patient's skin, blood from the wound site directly deposits into the fill area of the strip 19 located within the particular module 713. Once an adequate blood sample has reached the reaction area of the test strip 19, the monitor measures the working current present on strip 19 and, in turn, calculates the concentration of the particular analyte in the blood sample using the measured working current. The results of the calculation are preferably shown on a digital display on the monitor.

Upon completion of the assay, the monitor preferably rotates cartridge 711 one increment so that the next successive module 713 is available for a future test (to be performed in the same manner as described above). Cartridge 711 is preferably rotated, as needed, until all modules 713 are used. Once all modules 713 have been used, cartridge 711 is removed, discarded and replaced.

The embodiments shown in the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A unitary, disposable test cartridge capable of being removably coupled to a compatible analyte meter, said unitary, disposable cartridge comprising:
   (a) a base, the base including a top surface, a bottom surface, a front end, and a read end,
   (b) a cover secured to the base, whereby a substantially enclosed volume is formed, the cover including a top surface, a bottom surface, a front end and a rear end,
   (c) a lancet carrier disposed between the base and the cover in the substantially enclosed volume, the lancet carrier comprising a spring, the spring having a first end and a second end, the first end of the spring being fixedly coupled to the base, the second end of the spring capable of displacement relative to the first end,
   (d) a lancet removably mounted on the lancet carrier, and
   (e) an analyte test strip disposed between the base and the cover in the substantially enclosed volume, the analyte test strip having a first end, a second end and a plurality of electrodes, wherein the cover includes a window through which the plurality of electrodes is externally accessible, and
   (f) a skin receiving surface formed into the front end of said base in the form of an arcuate notch that extends inward from the front end of the base.

2. A unitary, disposable test cartridge capable of being removably coupled to a compatible analyte meter, said unitary, disposable cartridge comprising:
   (a) a base, the base including a top surface, a bottom surface, a front end, and a read end,
   (b) a cover secured to the base, whereby a substantially enclosed volume is formed, the cover including a top surface, a bottom surface, a front end and a rear end,
   (c) a lancet carrier disposed between the base and the cover in the substantially enclosed volume, the lancet carrier comprising a spring, the spring having a first end and a second end, the first end of the spring being fixedly coupled to the base, the second end of the spring capable of displacement relative to the first end,
   (d) a lancet removably mounted on the lancet carrier, and
   (e) an analyte test strip disposed between the base and the cover in the substantially enclosed volume, the analyte test strip having a first end, a second end and a plurality of electrodes, wherein the cover includes a window through which the plurality of electrodes is externally accessible, and
   (f) wherein an anchor is formed onto the first end of the spring, and
   (g) wherein the anchor is fixedly secured to the base, and
   (h) wherein a lancet support member is formed onto the second end of the spring, the lancet support member being slidably mounted on the base and capable of linear displacement relative to the anchor.

3. The unitary, disposable test cartridge as claimed in claim 1 wherein the lancet comprises:
(a) a tab adapted to be releasably retained on the lancet support member, and
(b) a sharpened needle formed onto the tab.

4. A unitary, disposable test cartridge capable of being removably coupled to a compatible analyte meter, said unitary, disposable cartridge comprising:
(a) a base, the base including a top surface, a bottom surface, a front end, and a read end,
(b) a cover secured to the base, whereby a substantially enclosed volume is formed, the cover including a top surface, a bottom surface, a front end and a rear end,
(c) a lancet carrier disposed between the base and the cover in the substantially enclosed volume, the lancet carrier comprising a spring, the spring having a first end and a second end, the first end of the spring being fixedly coupled to the base, the second end of the spring capable of displacement relative to the first end,
(d) a lancet removably mounted on the lancet carrier, and
(e) an analyte test strip disposed between the base and the cover in the substantially enclosed volume, the analyte test strip having a first end, a second end and a plurality of electrodes, wherein the cover includes a window through which the plurality of electrodes is externally accessible, and
(f) wherein said analyte test strip is adapted to be retained against the cover, and
(g) wherein the cover is shaped to define an opening along its front end through which a portion of the first end of the analyte test strip is externally visible.

5. A unitary, disposable test cartridge capable of being removably coupled to a compatible analyte test meter, said unitary disposable test cartridge comprising:
(a) a base, the base including a top surface, a bottom surface, a front end and a rear end,
(b) a lancet removably mounted on the base,
(c) an analyte test strip mounted on the base over the lancet, the analyte test strip comprising a first end, a second end and a plurality of electrodes, and
(d) a housing, the housing including a top surface, a bottom surface, a front end, a rear end and a pair of sidewalls that together define a substantially enclosed interior cavity, the interior cavity being sized and shaped to receive the base, the lancet and the analyte test strip, wherein a window is formed into the top surface of the housing through which window the plurality of electrodes is externally accessible.

6. The unitary, disposable test cartridge as claimed in claim 5 wherein the cartridge has a substantially flat, low profile design.

7. The unitary, disposable test cartridge as claimed in claim 6 wherein the top and bottom surfaces of the housing are flat.

8. The unitary, disposable test cartridge as claimed in claim 5 wherein an opening is formed into the front end of the housing, the opening being in communication with the interior cavity.

9. The unitary, disposable test cartridge as claimed in claim 8 wherein a skin receiving surface is formed into the front end of the base immediately surrounding the opening.

10. The unitary, disposable test cartridge as claimed in claim 5 wherein a shallow recess is formed into the top surface of the base, the shallow recess being sized and shaped to receive the lancet.

11. The unitary, disposable test cartridge as claimed in claim 5 wherein a spring is integrally formed into the base, the spring including a first end and a second end.

12. The unitary, disposable test cartridge as claimed in claim 11 wherein the first end of the spring is fixed in place and wherein the second end of the spring is capable of displacement relative to the first end of the spring.

13. The unitary, disposable test cartridge as claimed in claim 12 wherein the lancet is mounted on the second end of the spring.

14. The unitary, disposable test cartridge as claimed in claim 13 wherein the lancet is substantially flat and includes a sharpened needle.

15. An analyte test device which is adapted to be removably coupled to a compatible analyte test meter, said analyte test device comprising:
(a) a housing shaped to define an interior cavity,
(b) a lancet slidably mounted within the interior cavity of said housing, said lancet comprising a sharpened tip, the sharpened tip being adapted to selectively penetrate outside of the interior cavity of said housing, and
(c) an analyte test strip disposed within the interior cavity of said housing at an acute angle relative to said lancet, said analyte test strip comprising a first end, a second end and a plurality of electrodes, and
(d) wherein said housing includes a generally cylindrical sidewall which defines the interior cavity, the sidewall comprising an inner surface, an outer surface, an open bottom end and an open top end, and
(e) wherein said analyte test strip is fixedly mounted onto the inner surface of the sidewall, the first end of said analyte test strip being spaced in from the open bottom end of said housing, and
(f) wherein a needle support is integrally formed onto the inner surface of said housing, the needle support being shaped to define a longitudinal bore which is sized and shaped to receive at least a portion of said lancet, and
(g) further comprising a spring for resiliently urging said the tip of said lancet away from the open bottom end of said housing, said spring including a first end and a second end, and
(h) further comprising a cap, said cap being fixedly mounted on said lancet, and
(i) wherein the spring is mounted axially over the lancet with the first end of the spring disposed against the needle support in the housing and the second end of the spring disposed against the cap.

* * * * *